(12) United States Patent
Bushman

(10) Patent No.: US 8,752,579 B2
(45) Date of Patent: *Jun. 17, 2014

(54) CHECK VALVE FOR FLUID INJECTOR

(75) Inventor: Richard Paul Bushman, Stillwater, MN (US)

(73) Assignee: RJC Products LLC, Lake Elmo, MN (US)

( * ) Notice: Subject to any disclaimer, the term of this patent is extended or adjusted under 35 U.S.C. 154(b) by 1071 days.

This patent is subject to a terminal disclaimer.

(21) Appl. No.: 11/751,803

(22) Filed: May 22, 2007

(65) Prior Publication Data
US 2008/0289696 A1    Nov. 27, 2008

(51) Int. Cl.
*F16K 15/14* (2006.01)
*A61C 1/16* (2006.01)
*A61C 17/06* (2006.01)

(52) U.S. Cl.
CPC . *A61C 1/16* (2013.01); *A61C 17/04* (2013.01); *F16K 15/144* (2013.01); *A61C 17/043* (2013.01)
USPC .............................. 137/527; 137/852; 604/247

(58) Field of Classification Search
USPC ........... 137/515.5, 527, 527.4, 843, 852, 855, 137/856, 857, 859; 251/331; 433/116, 229, 433/95; 604/247, 902
See application file for complete search history.

(56) References Cited

U.S. PATENT DOCUMENTS

| | | | |
|---|---|---|---|
| 2,378,613 A | 6/1945 | Young et al. | |
| 2,670,757 A | 3/1954 | Delany | |
| 2,707,965 A | 5/1955 | Allen | |
| 2,851,054 A | 9/1958 | Campbell et al. | |
| 2,864,394 A | 12/1958 | Hempel | |
| 2,867,213 A | 1/1959 | Thomas, Jr. | |
| 3,292,658 A * | 12/1966 | Scaramucci | 137/856 |
| 3,417,750 A | 12/1968 | Carson | |
| 3,463,159 A | 8/1969 | Heimlich | |
| 3,570,525 A | 3/1971 | Borsum et al. | |
| 3,572,375 A | 3/1971 | Rosenberg | |
| 3,626,980 A | 12/1971 | Svensson | |

(Continued)

FOREIGN PATENT DOCUMENTS

EP       0 546 223 A1    6/1993

OTHER PUBLICATIONS

Invitation to Pay Additional Fees with Partial International Search mailed Sep. 12, 2008 23552 Patent Trademark Office.

*Primary Examiner* — Kevin Lee
*Assistant Examiner* — P. Macade Nichols
(74) *Attorney, Agent, or Firm* — Holland & Hart LLP

(57) ABSTRACT

A backflow-prevention system that substantially prevents contaminant backflow at a treatment site. The system includes a fluid ejector tube for insertion into the patient's mouth and for removal of fluids when a threshold vacuum pressure is applied. A backflow prevention device receives fluid from the fluid ejector tube and includes an internally positioned valve. The valve prevents contaminant backflow upon release of the vacuum pressure or a reduction in the vacuum pressure. Upon application of vacuum pressure, the valve moves into an open position to allow fluid flow away from the treatment site. The system can also include a disposable cover member that extends over at least portions of the fluid ejector tip, the backflow prevention device, and other features such as an ON/OFF valve assembly of a suction system. Similar principles of backflow prevention can be applied to fluid dispensers (e.g., liquid soap dispensers) wherein prevention of backflow of the fluid into the fluid storage container is necessary, in order for the dispenser to function properly.

32 Claims, 17 Drawing Sheets

(56) References Cited

U.S. PATENT DOCUMENTS

| | | | |
|---|---|---|---|
| 3,628,565 A | 12/1971 | McWethy | |
| 3,807,444 A * | 4/1974 | Fortune | 137/512.1 |
| 3,910,283 A | 10/1975 | Leveen | |
| 4,009,366 A * | 2/1977 | Danell | 219/208 |
| 4,081,176 A | 3/1978 | Johnson | |
| 4,083,115 A | 4/1978 | McKelvey | |
| 4,160,383 A | 7/1979 | Rauschenberger | |
| 4,232,677 A | 11/1980 | Leibinsohn | |
| 4,286,622 A | 9/1981 | Ninomiya et al. | |
| 4,405,316 A * | 9/1983 | Mittleman | 604/86 |
| 4,474,209 A | 10/1984 | Akhtarekhavari | |
| 4,538,508 A * | 9/1985 | Ballard | 454/361 |
| 4,556,086 A | 12/1985 | Raines | |
| 4,610,275 A | 9/1986 | Beecher | |
| 4,610,276 A * | 9/1986 | Paradis et al. | 137/856 |
| 4,683,916 A | 8/1987 | Raines | |
| 4,723,912 A * | 2/1988 | Nieusma | 433/116 |
| 4,735,607 A | 4/1988 | Keith, Jr. | |
| 4,758,224 A | 7/1988 | Siposs | |
| 4,810,194 A * | 3/1989 | Snedden | 433/91 |
| 4,904,236 A | 2/1990 | Redmond et al. | |
| 4,966,551 A | 10/1990 | Betush | |
| 4,998,880 A | 3/1991 | Nerli | |
| 5,044,953 A | 9/1991 | Sullivan | |
| 5,114,342 A | 5/1992 | Young et al. | |
| 5,158,539 A | 10/1992 | Kolff et al. | |
| 5,165,891 A | 11/1992 | Young et al. | |
| 5,176,658 A * | 1/1993 | Ranford | 604/247 |
| 5,242,398 A * | 9/1993 | Knoll et al. | 604/103.05 |
| 5,267,586 A | 12/1993 | Jankavaara | |
| 5,295,478 A | 3/1994 | Baldwin | |
| 5,295,830 A | 3/1994 | Shen et al. | |
| 5,413,142 A * | 5/1995 | Johnson et al. | 137/515.5 |
| 5,425,637 A | 6/1995 | Whitehouse et al. | |
| 5,441,410 A | 8/1995 | Segerdal | |
| 5,453,097 A | 9/1995 | Paradis | |
| 5,464,350 A | 11/1995 | Bierbaum | |
| 5,464,397 A | 11/1995 | Powers Jr. | |
| 5,509,802 A | 4/1996 | Whitehouse et al. | |
| 5,520,041 A | 5/1996 | Haswell | |
| 5,535,785 A | 7/1996 | Werge et al. | |
| 5,725,374 A | 3/1998 | Young | |
| 5,855,478 A | 1/1999 | Van | |
| 5,921,776 A * | 7/1999 | Heilbrunn | 433/116 |
| 5,971,723 A | 10/1999 | Bolt et al. | |
| 5,992,462 A * | 11/1999 | Atkinson et al. | 137/854 |
| 6,089,272 A | 7/2000 | Brand et al. | |
| 6,203,321 B1 | 3/2001 | Helmer et al. | |
| 6,364,861 B1 | 4/2002 | Feith et al. | |
| 7,131,839 B2 | 11/2006 | March | |
| 2005/0085746 A1 * | 4/2005 | Adams et al. | 600/585 |

\* cited by examiner

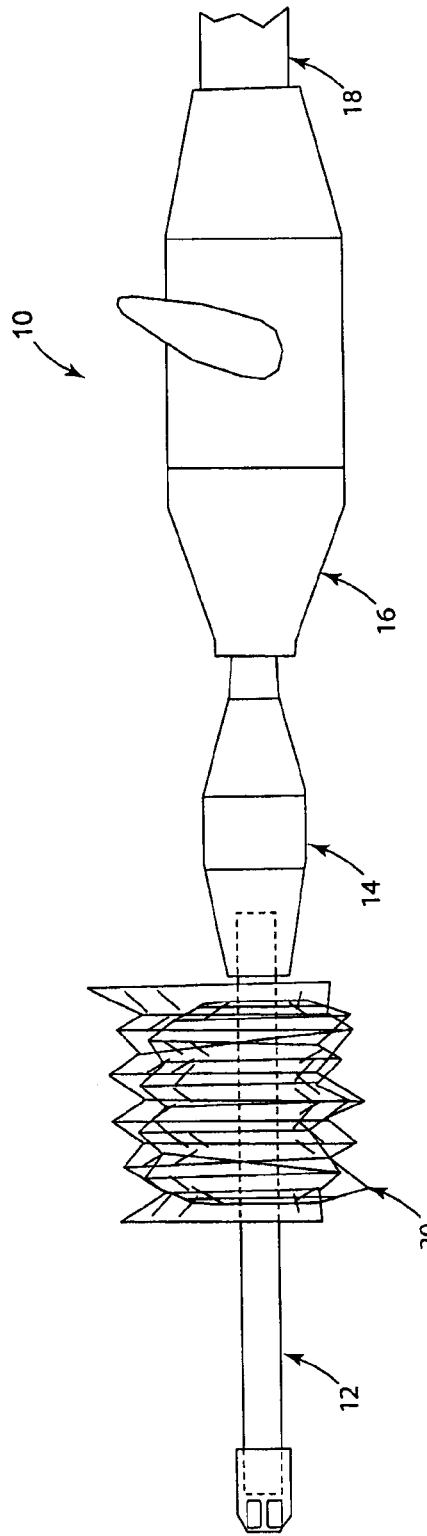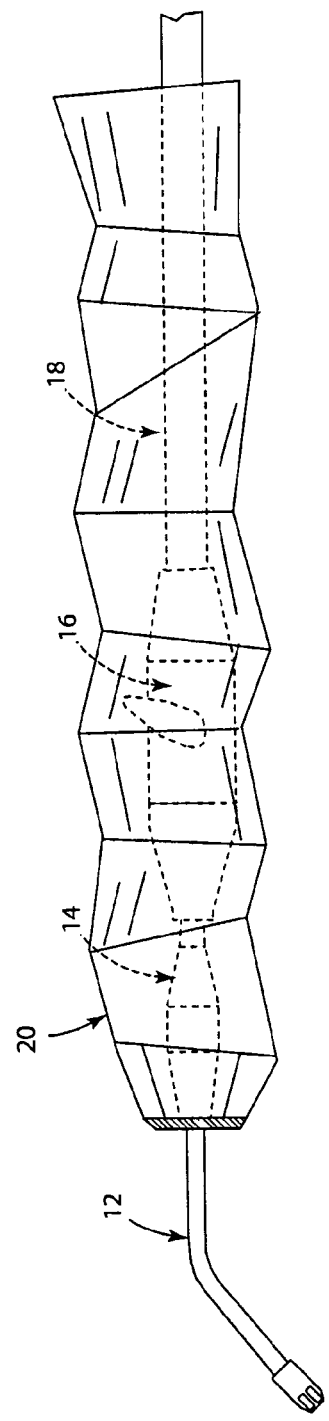
FIG. 1
FIG. 2

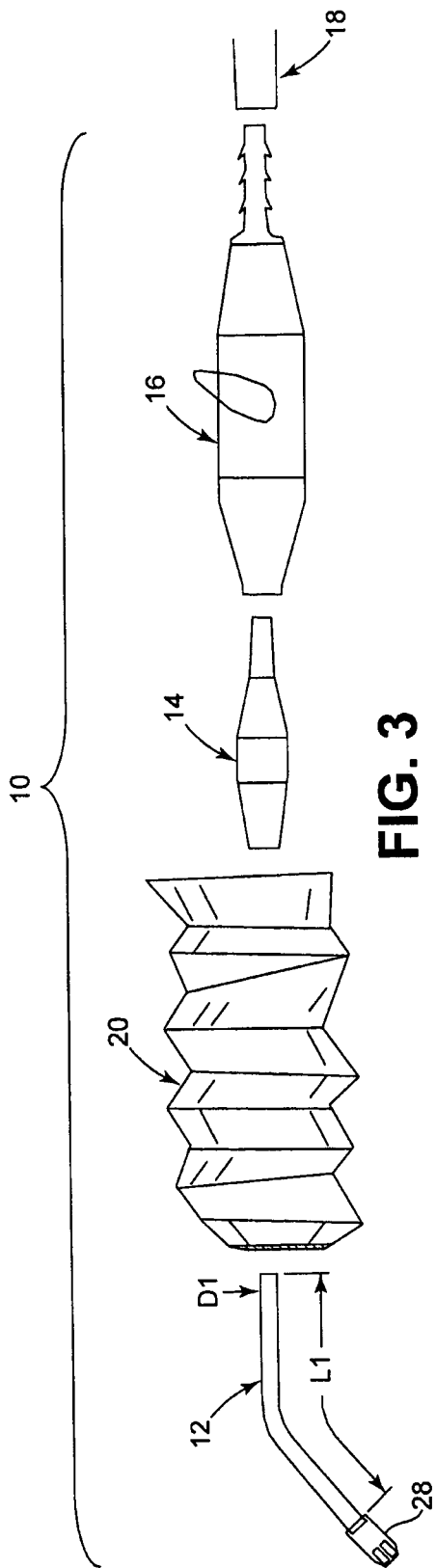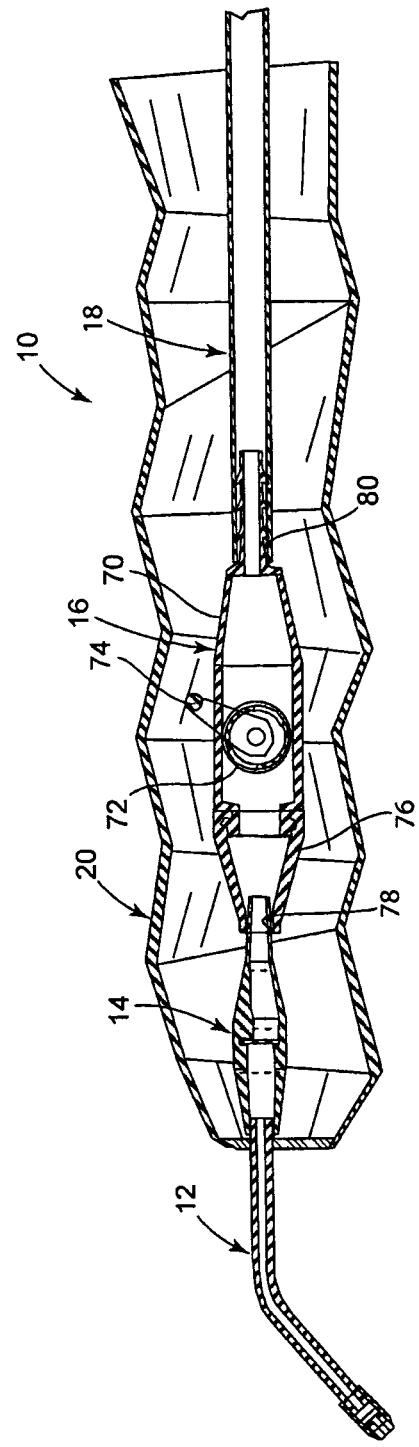

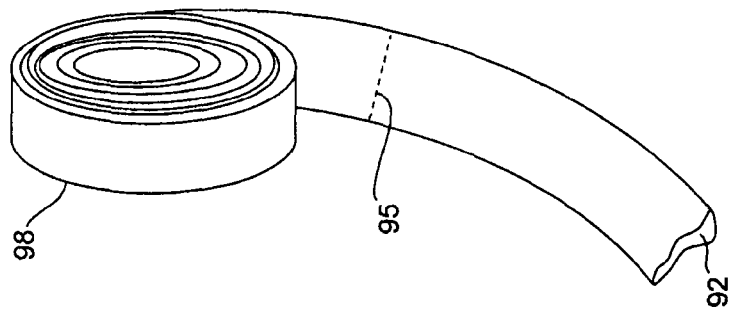
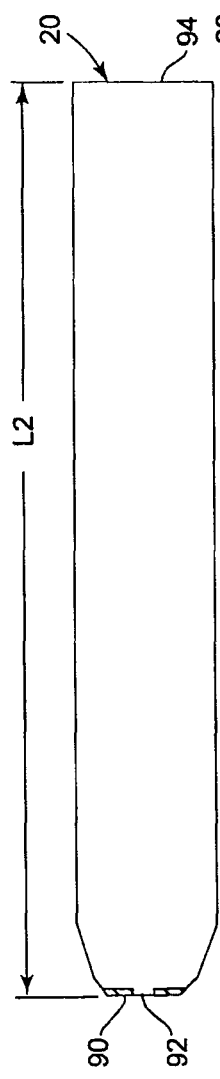
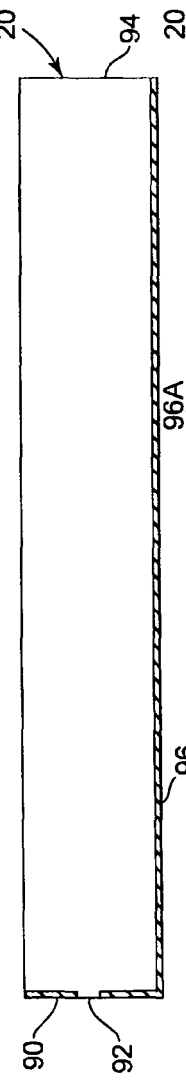
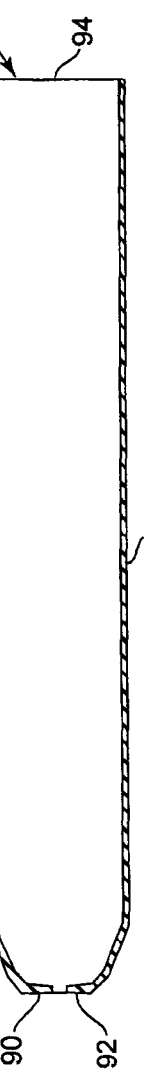
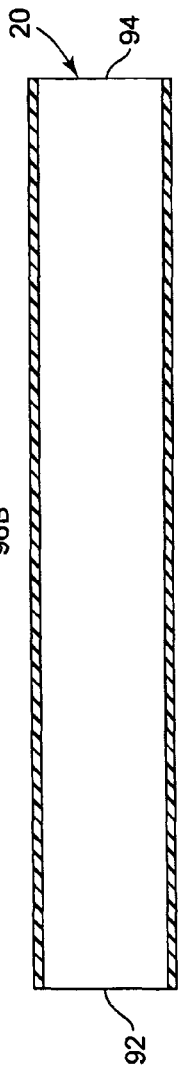

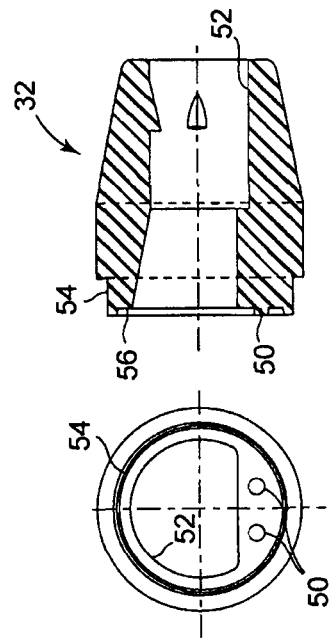
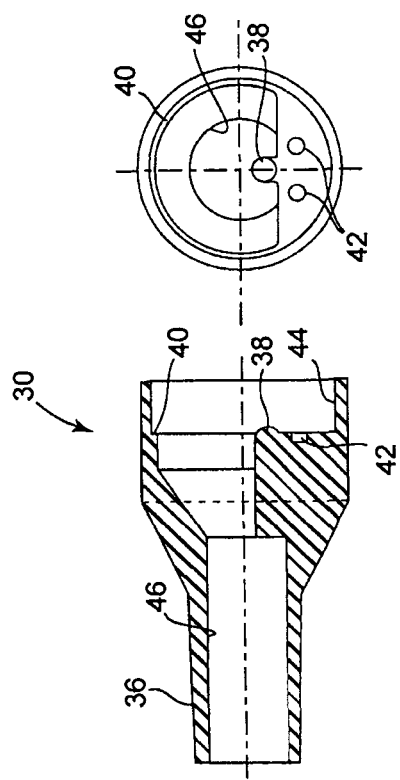

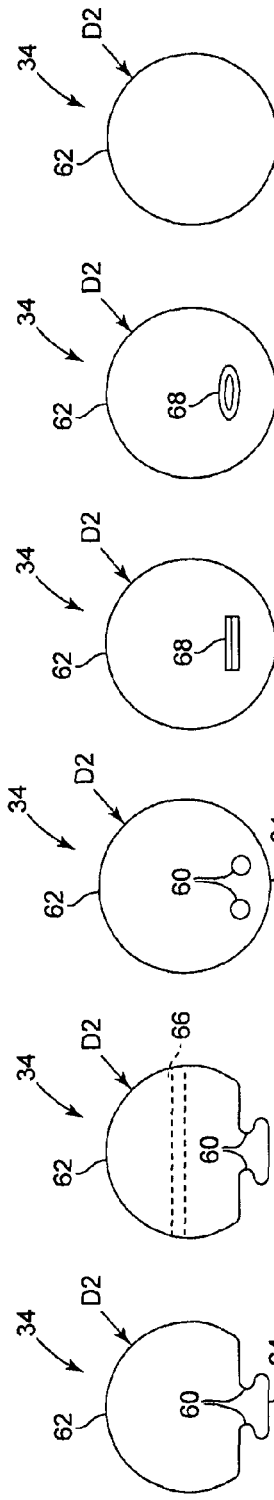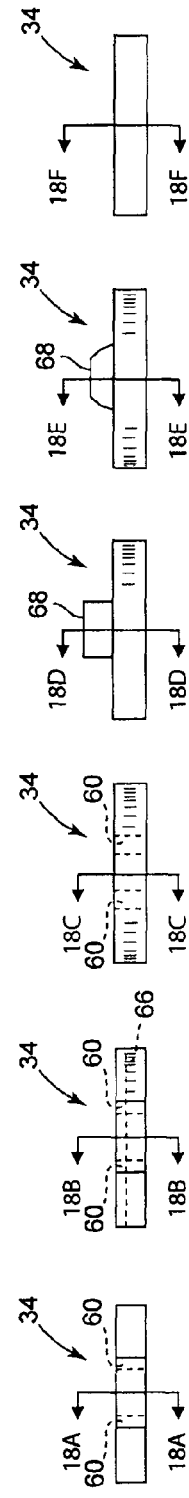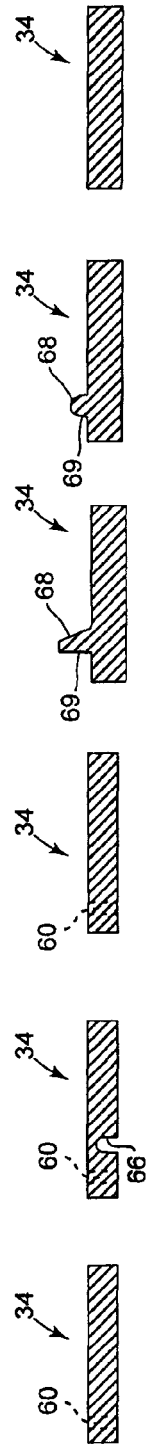

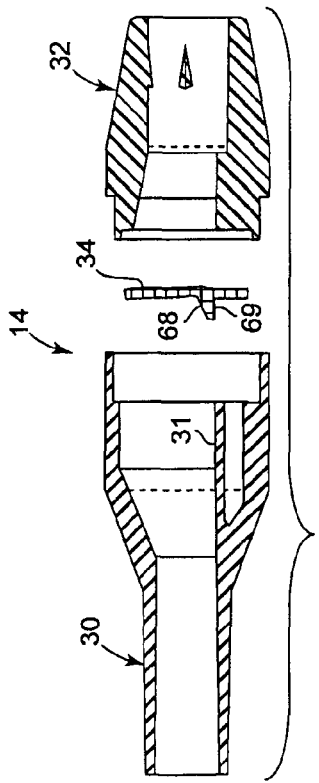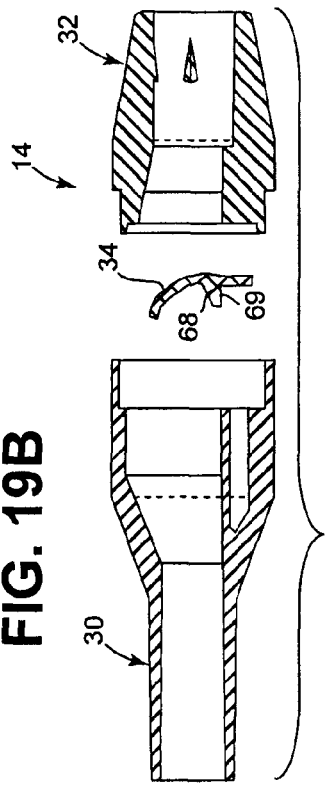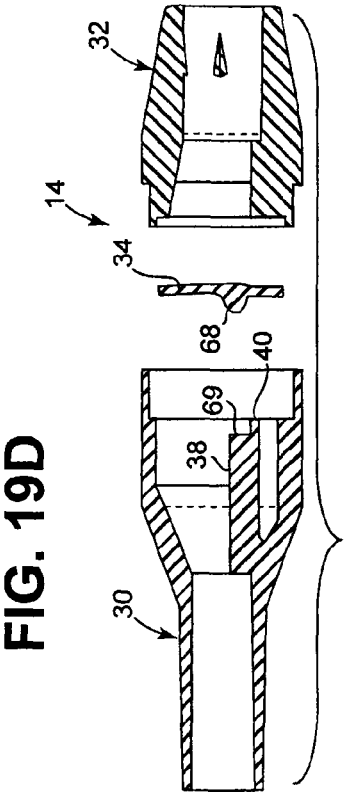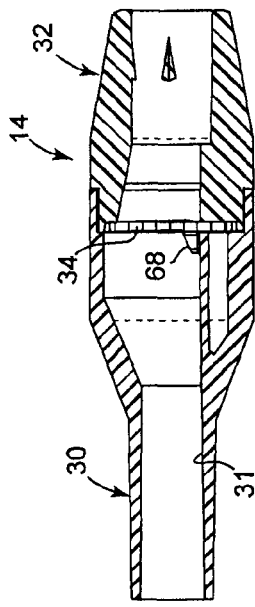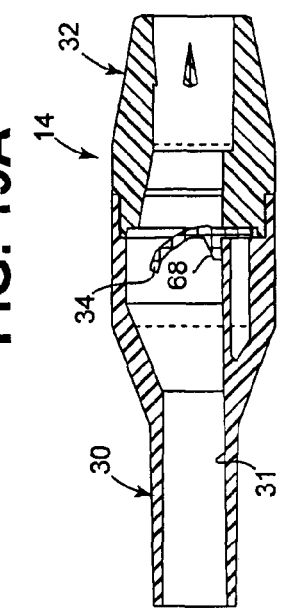

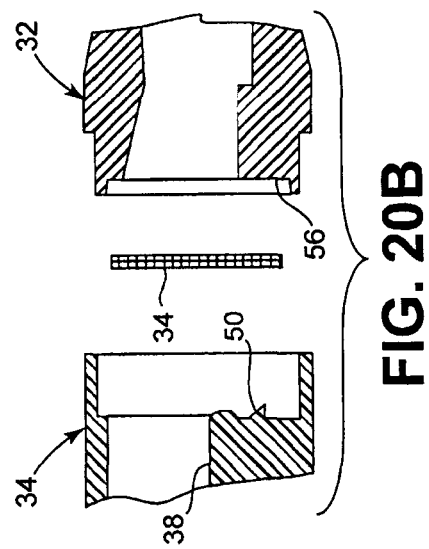
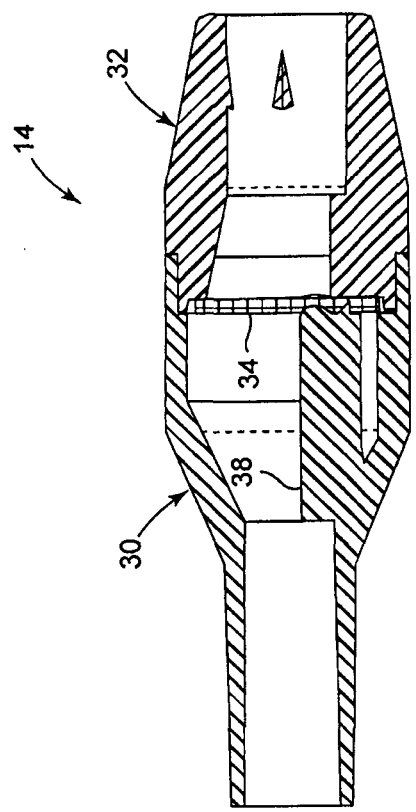
FIG. 20B
FIG. 20A

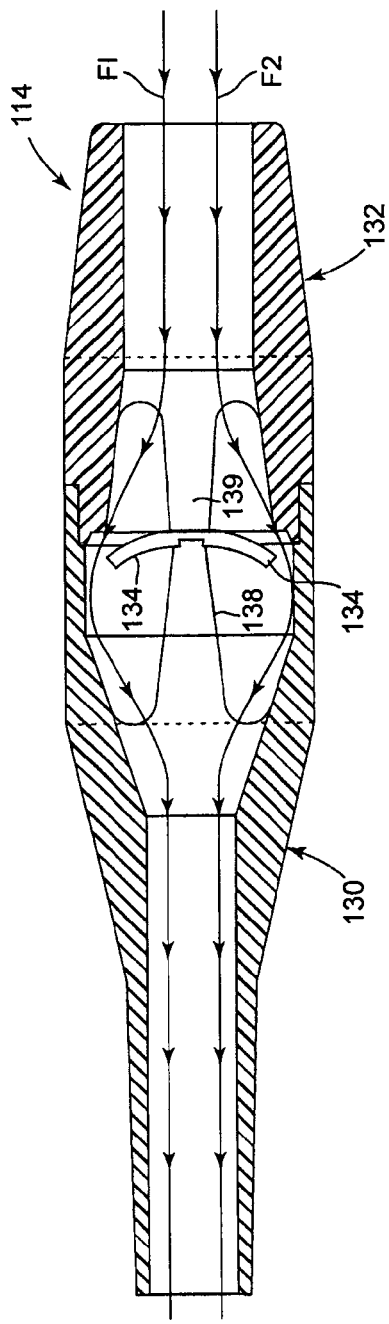
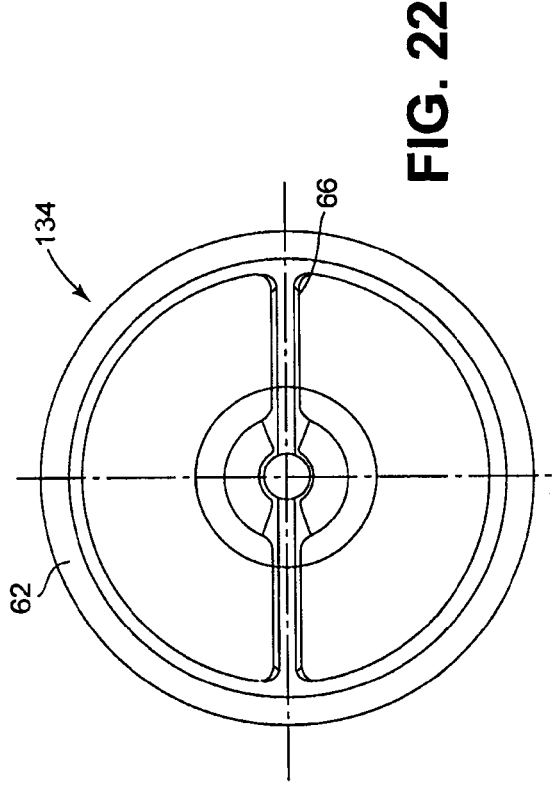
FIG. 23
FIG. 22

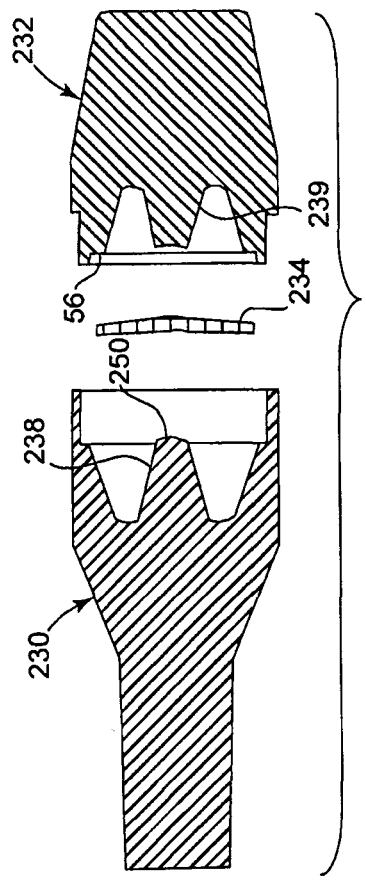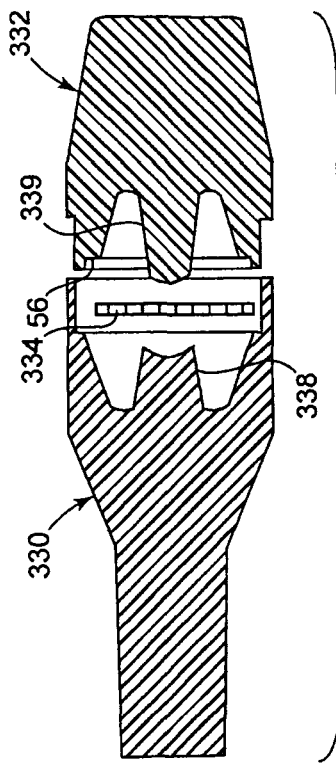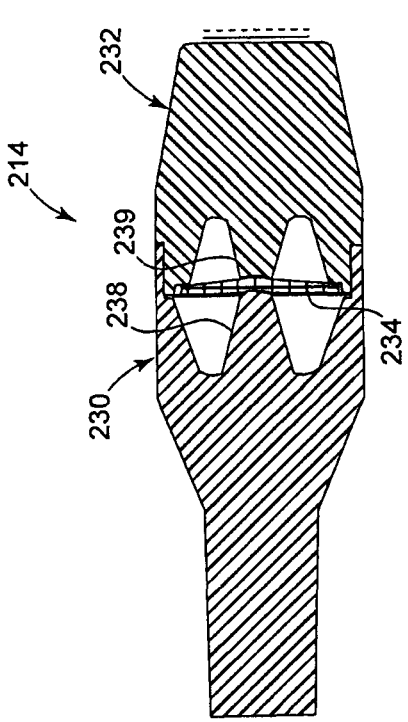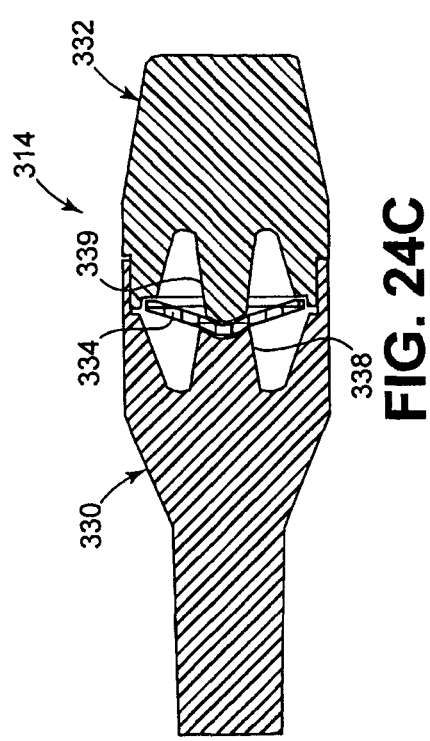

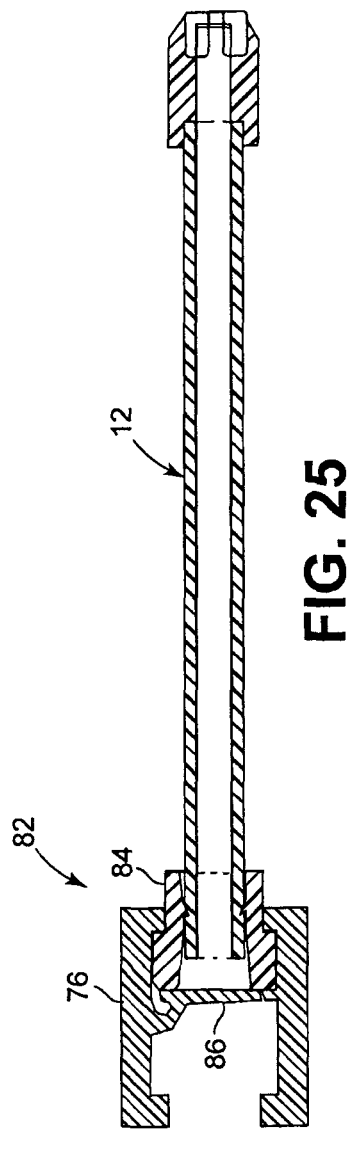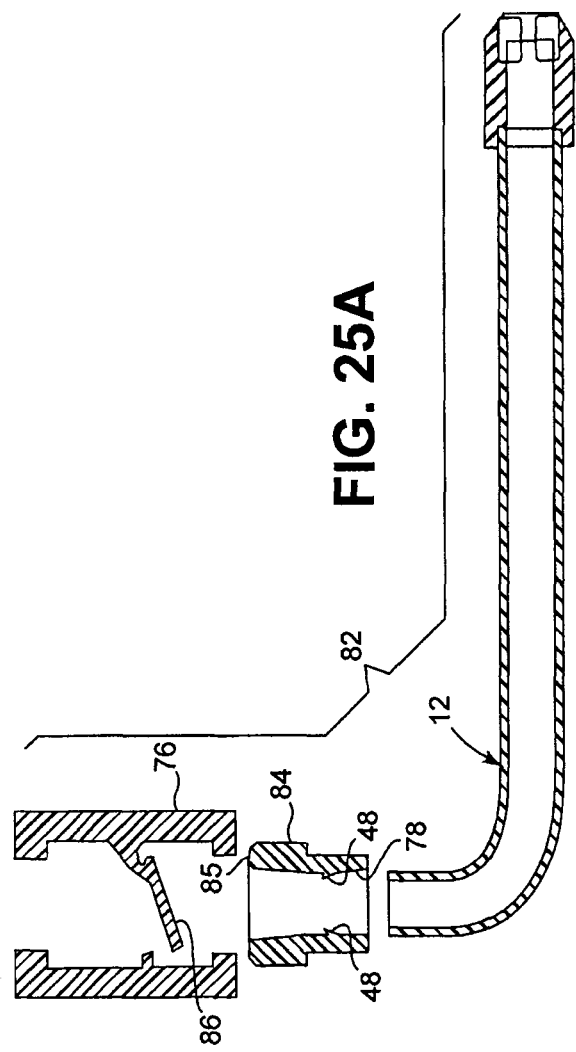

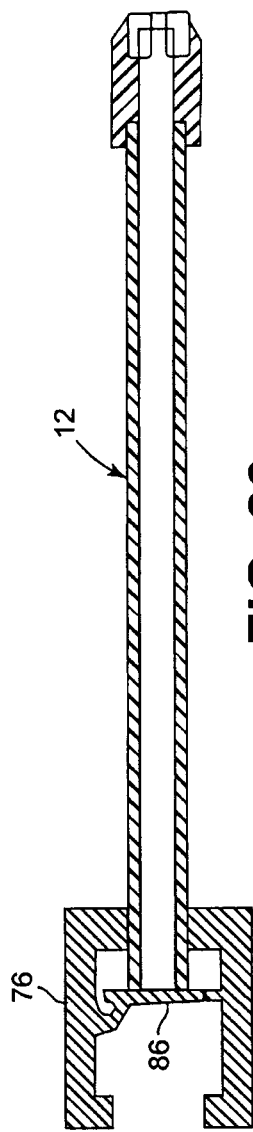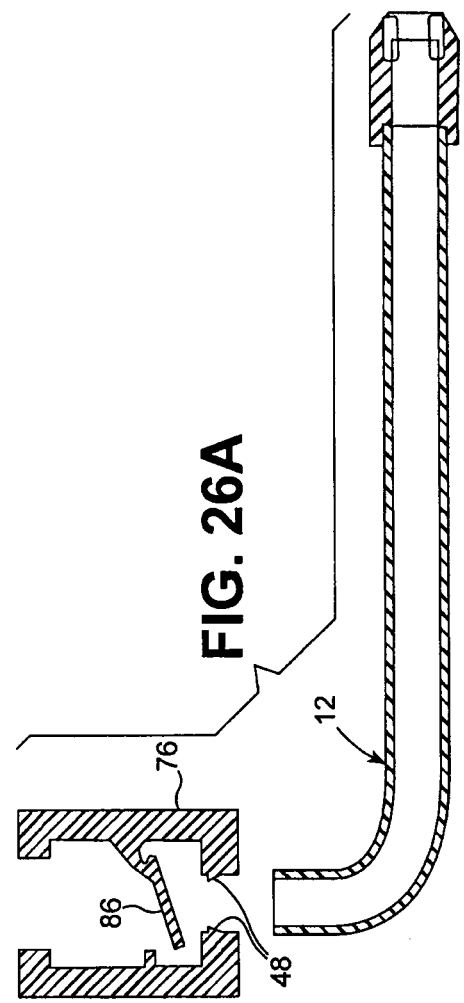

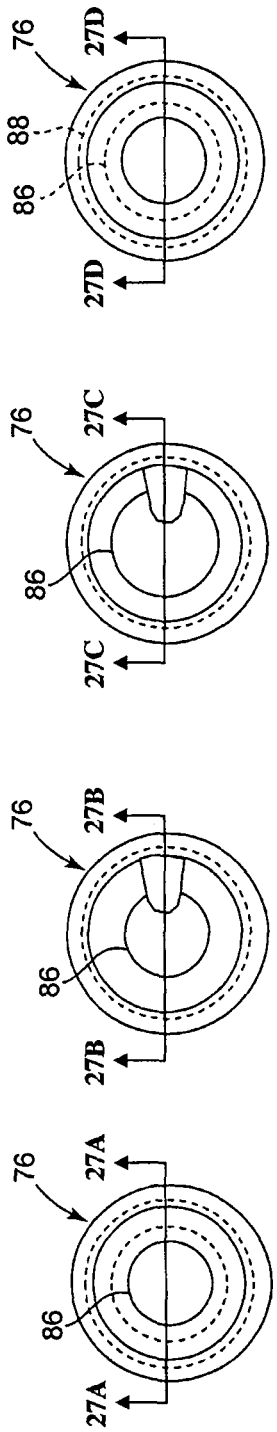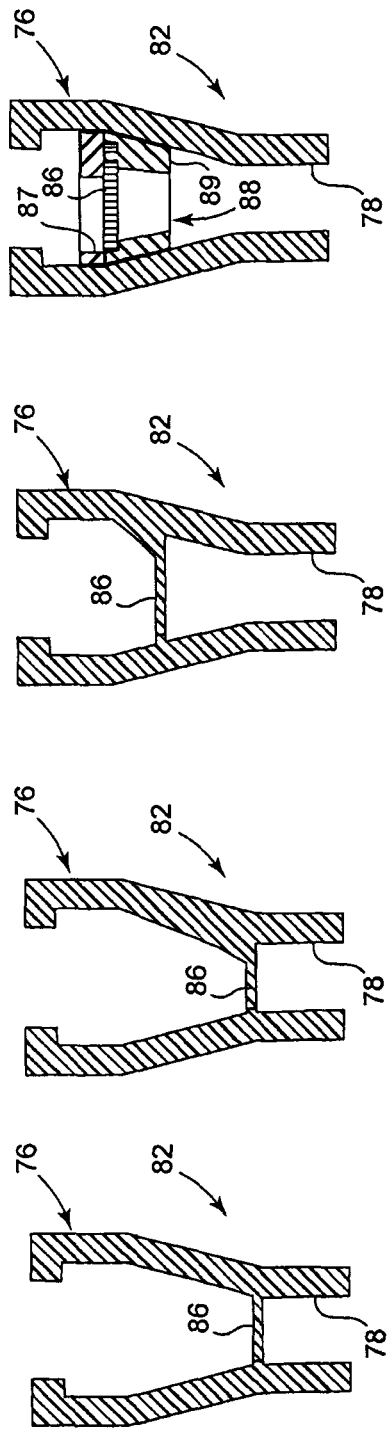

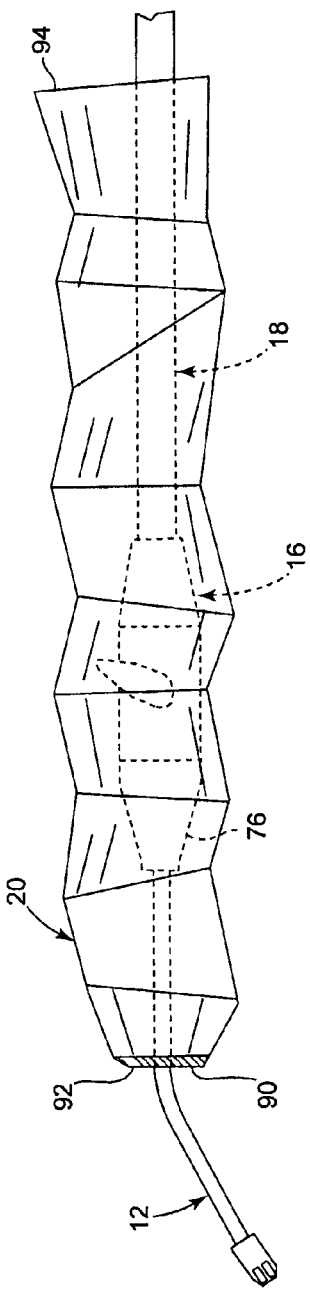
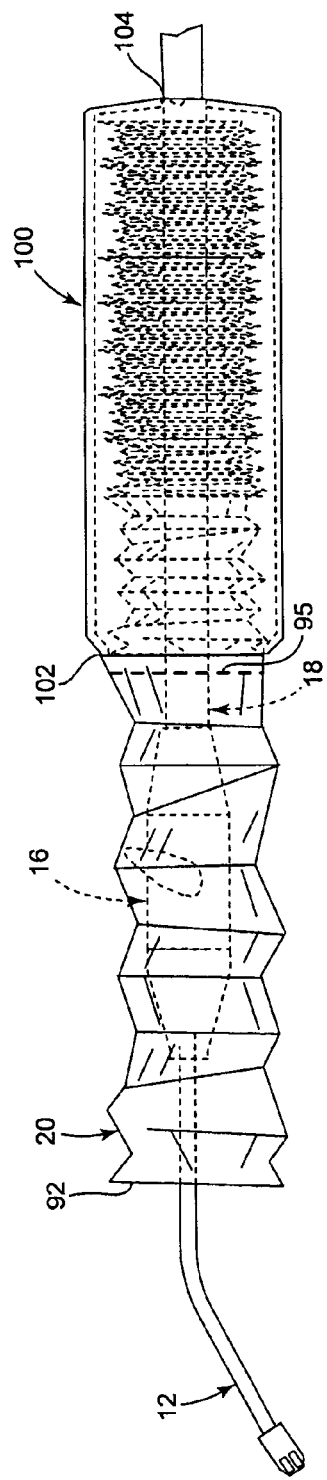
FIG. 29
FIG. 30

CHECK VALVE FOR FLUID INJECTOR

TECHNICAL FIELD

The present disclosure generally relates to suctioning device, and more particularly to medical suctioning devices that are adapted to inhibit backflow of suctioned materials in the suctioning device.

BACKGROUND

Cross-contamination between patients, for example, dental patients, can occur when suctioning devices attached to vacuum lines are used to remove various bodily and/or externally introduced fluids. Although the disposable distal ends of these devices typically are changed between patients, the vacuum lines employed typically are not changed. Saliva, blood and other contaminants pass from the distal end into the vacuum line, where they can remain until arrival of the next patient. When a new distal end is inserted onto the vacuum line for a new patient, contaminants from the previous patient can backflow from the vacuum line into the distal end and enter the patient's mouth, for example. Clearly, with the growing concerns over infections like the Bird Flu and the incidence of AIDS, Hepatitis and other communicable diseases, this is a situation to be avoided.

A number of prior art devices have attempted to prevent backflow and the resulting likelihood of cross-contamination between patients. U.S. Pat. Nos. 5,425,637 and 5,509,802 to Whitehouse, et al. and U.S. Pat. No. 5,464,397 to Powers, Jr., which are incorporated herein by reference, disclose prior art attempts to prevent or at least minimize contaminant backflow and cross-contamination. The two Whitehouse patents disclose suction lines having vacuum-release apertures through a tubular sidewall of a saliva ejector tip. If a patient closes his or her lips around the tip, the vacuum-release aperture is said to prevent creation of a temporary high vacuum in the patient's mouth; the aperture also likely prevents stoppage of air and/or fluid, at least between the aperture and the rest of the system. The Powers, Jr. patent, on the other hand, appears to rely merely on a "tortuous path" within the device to substantially prevent backflow of bacteria.

However, as recent studies are believed to have shown, a boundary layer can form around the internal circumference of many currently used suctioning devices. The boundary layer is the portion of air and/or other fluid flowing in the immediate vicinity of the internal circumference. Flow at the boundary layer is severely reduced, even eliminated due to the forces of adhesion and viscosity caused by the internal circumference. Because suction within the boundary layer is reduced or eliminated, a "bio-film" can be created, allowing saliva, blood and other contaminants to flow by gravity, for example, from the main vacuum system of a dental office, through saliva ejector assemblies and into the mouths of patients.

It is not believed that prior art suctioning devices adequately account for or address backflow caused by boundary layer conditions, and/or other conditions such as mouth-induced backflow suction. Prior art devices thus allow an unacceptably high likelihood of cross-contamination between patients. Clearly, a need has arisen for a solution to this problem.

SUMMARY

One aspect of the present disclosure relates to a backflow-prevention system that can substantially prevent contaminant backflow from a vacuum device into a patient's mouth. The system in accordance with the present disclosure includes a fluid ejector tube for insertion into the patient's mouth and for removal of saliva, blood, etc. when a vacuum is applied by a vacuum device. A backflow-prevention device receives fluid from the fluid ejector tube and includes an internal valve seat. Valve componentry disposed within the backflow-prevention device includes a housing and a valve flap operably supported by the housing to engage the valve seat and prevent contaminant backflow upon release of the vacuum. Upon application of a vacuum condition, the valve flap automatically disengages from the valve seat and allows fluid flow away from the patient's mouth. The valve flap can be functionally flexible for movement within the housing away from the valve seat, and/or is biased toward the valve seat upon release of the vacuum. Corresponding devices and methods provide similar advantages.

Another aspect of the present disclosure relates to disposable covers that can be used to cover all or portions of the ejector tube, backflow prevention device, ON/OFF valve, and vacuum devices in a suction assembly. The disposable cover provides a sanitary barrier between the operator and those features positioned within the disposable cover. The disposable cover can be assembled as a single unit with, for example, the ejector tube and backflow prevention device, or with the ejector tube alone so that replacement of the ejector tube results in replacement of the disposable cover.

The above summary is not intended to describe each disclosed embodiment or every implementation of the inventive aspects disclosed herein. Figures in the detailed description that follow more particularly describe features that are examples of how certain inventive aspects may be practiced. While certain embodiments are illustrated and described, it will be appreciated that disclosure is not limited to such embodiments.

BRIEF DESCRIPTION OF THE DRAWINGS

FIG. 1 is a schematic side view of an example suction system in accordance with the present disclosure.

FIG. 2 is a schematic side view of the example suction system shown in FIG. 1 with the cover member positioned on the ejector tube.

FIG. 3 is schematic exploded side view of the example suction system shown in FIG. 1.

FIG. 4 is a schematic cross-sectional side view of the example suction system shown in FIG. 1.

FIGS. 8A-D are schematic cross-sectional side views showing example cover members in accordance with the present disclosure.

FIG. 9 is a schematic perspective view showing continuous length cover member in a rolled up state.

FIG. 12 is a schematic cross-sectional side view of the proximal housing portion of the backflow device shown in FIG. 10.

FIG. 13 is a schematic end view of the proximal housing portion shown in FIG. 12.

FIG. 14 is a schematic cross-sectional side view of the distal housing portion of the backflow device shown in FIG. 10.

FIG. 15 is a schematic end view of the distal housing portion shown in FIG. 12.

FIGS. 16A-F are schematic front views of several example valve flaps for use with the backflow devices shown herein.

FIGS. 17A-F are schematic bottom views of the example valve flaps shown in FIGS. 16A-E.

FIGS. 18A-F are schematic cross-sectional side views of the valve flaps shown in FIGS. 16A-E.

FIG. 19A is a schematic cross-sectional side view of another example backflow device in accordance with the present disclosure, wherein the valve flap is in a closed state.

FIG. 19B is a schematic exploded cross-sectional side view of the backflow device shown in FIG. 19A.

FIG. 19C is a schematic cross-sectional side view of the example backflow device shown in FIG. 19A, wherein the valve flap is in an open state.

FIG. 19D is a schematic exploded cross-sectional side view of the backflow device shown in FIG. 19C.

FIG. 20A is a schematic cross-sectional side view of another example backflow device in accordance with the present disclosure, wherein the connection protrusion includes a barb construction.

FIG. 20B is a schematic exploded cross-sectional side view of the backflow device shown in FIG. 20A.

FIG. 21A is a schematic cross-sectional side view of another example backflow device in accordance with the present disclosure, wherein the valve flap is in a closed state.

FIG. 21B is a schematic exploded cross-sectional side view of the backflow device shown in FIG. 21A.

FIG. 22 is a schematic front view of another example valve flap in accordance with the present disclosure, wherein the valve flap is bendable about a lateral centerline.

FIG. 23 is a schematic cross-sectional side view showing fluid flow through another example backflow device that includes the valve flap of FIG. 22.

FIG. 24A is a schematic cross-sectional side view of another example backflow device in accordance with the present disclosure, wherein the biasing protrusion includes a connection protrusion.

FIG. 24B is a schematic exploded cross-sectional side view the example backflow device shown in FIG. 24A.

FIG. 24C schematic cross-sectional side view of another example backflow device in accordance with the present disclosure, wherein biasing protrusion and retention protrusion are shaped to bias the valve flap in a closed state.

FIG. 24D is a schematic exploded cross-sectional side view the example backflow device shown in FIG. 24C.

FIG. 25 is a schematic cross-section side view of an example assembly in accordance with the present disclosure, wherein the assembly includes an ejector tube and an ON/OFF valve boot, the boot including a backflow valve member.

FIG. 25A is a schematic exploded cross-sectional side view of the assembly shown in FIG. 25.

FIG. 26 is a schematic cross-section side view of another example assembly in accordance with the present disclosure, wherein the assembly includes an ejector tube and an ON/OFF valve boot, the boot including a backflow valve member.

FIG. 26A is a schematic exploded cross-sectional view of the assembly shown in FIG. 26.

FIGS. 27A-D are schematic cross-sectional side views of several example ON/OFF valve boots having a backflow valve member in accordance with the present disclosure.

FIGS. 28A-D are schematic end views of the ON/OFF valve boots shown in FIGS. 27A-D.

FIG. 29 is a schematic side view of another example assembly in accordance with the present disclosure, wherein the assembly includes an ON/OFF valve, an ejector tube, and a cover member.

FIG. 30 is a schematic side view of another example assembly in accordance with the present disclosure, wherein the assembly includes an ON/OFF valve, an ejector tube, and a cover member, the cover member being drawn from a continuous cover member that is housed proximal of the ON/OFF valve.

DETAILED DESCRIPTION

Figure 7:
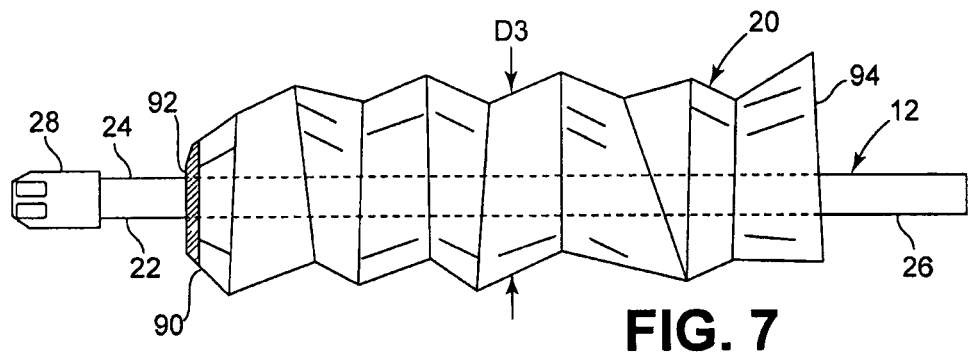
FIG. 7 is a schematic side view of another example assembly in accordance with the present disclosure that includes an ejector tube and cover.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The following discussion is intended to provide a brief, general description of a suitable environment in which the invention may be implemented. Although not required, the invention will be described in the general context of vacuum suction devices, for example, a dental saliva ejector device. The structure, creation, and use of some example dental fluid ejector devices are described hereinafter.

The example embodiments disclosed herein have wide application to a number of medical procedures and environments. Suction is often used in dental applications, as described above. Suctioning devices are also typically used to drain fluid and remove blood from many surgical environments, aid in respiration, and aid in a number of other medical and surgical procedures. Additionally, suctioning devices in which cross-contamination is undesirable are used in non-medical and non-surgical environments, such as in some types of liquid dispensers where preventing backflow of a fluid is required. Therefore, while most of the embodiments described with reference to the attached figures are directed to dental devices and applications, many other applications and related embodiments are envisioned.

The Example Suction Assemblies of FIGS. 1-24

Several example suction assemblies 10 are described now with reference to FIGS. 1-24D. The suction assembly 10 includes an ejector tube assembly 12, a backflow prevention assembly 14, an ON/OFF valve assembly 16, a vacuum hose 18, and a cover member 20. These features are shown in the exploded view of FIG. 3 and in further detail in the cross-sectional view of FIG. 4. The features 12, 14, 16, 18, 20 can be combined as separate subassemblies that are coupled together at the point of use where, for example, a patient is being treated by the suction assembly 10. In one example, the ejector tube assembly 12 and cover member 20 are arranged as a subassembly that is later connected to the backflow prevention assembly 14, or in alternative embodiments connected directly to the ON/OFF valve assembly 16. In another example arrangement, the ejector tube assembly 12, backflow prevention assembly 14, and cover member 20 are provided as a subassembly that is removably engaged with the ON/OFF valve assembly 16. Other subassembly arrangements are possible, some of which are described in further detail below.

The ejector tube assembly 12 includes an ejector tube 22, having distal and proximal ends 24, 26, an outer diameter D1, a length L1, and an ejector tip 28 (see FIG. 3). The ejector tube 22 can be referenced as, for example, a fluid or liquid ejector tube, a saliva ejector tube, a particle ejector tube, or a fluid source tube. The ejector tube 22 can have a contoured shape. The contoured shape of the ejector tube 22 can be preformed. In some arrangements, the ejector tube assembly 12 can include a stiffening member such as a wire that extends along at least a portion of the length of the tube 22 that provides adjustability of the contoured shape and retention of that shape due to the inherent stiffness of the stiffening member. The outer diameter D1 is typically sized to provide insertion of the proximal end 26 into the distal end of the backflow prevention assembly 14. The ejector tip 28 can have various constructions that provide proper fluid flow into the ejector tube assembly 12.

The backflow prevention assembly 14 includes a proximal housing portion 30, a distal housing portion 32, and a valve flap 34. Other example backflow prevention assemblies are disclosed in co-owned U.S. Pat. No. 6,203,321, which is incorporated herein by reference. Many of the embodiments disclosed in U.S. Pat. No. 6,203,321 require a plurality of components used in the valving structure within the backflow prevention assembly. Further, many of the examples disclosed in U.S. Pat. No. 6,203,321 include valving components that are molded, which can increase the complexity and cost associated with generating those valving components.

Referring now to FIGS. 10-21B, the proximal housing portion 30 includes a neck portion 36, a biasing protrusion 38, a first mating surface 40, a pair of connection recesses 42, a second mating surface 44, and a flow orifice 46. The proximal housing portion 30 can also include a plurality of barbed members (e.g., barbs 48 that are shown positioned interior of the distal housing portion 32) that can be positioned on an exterior of the neck portion 36 to help retain the backflow prevention assembly 14 in engagement with the ON/OFF valve assembly 16.

The biasing protrusion 38 is positioned vertically above (e.g., radially inward toward a central axis of the proximal housing portion 30) the connection recesses 42. A distal end of the biasing protrusion 38 extends distally in the axial direction beyond the first mating surface 40 (see FIG. 12).

The biasing protrusion 38 exerts an axially directed force upon the valve flap 34 when the backflow prevention assembly 14 is assembled to bias the valve flap 34 toward a valve seat 56 of the distal housing portion 32. The biasing protrusion 38 applies a biasing force to the valve flap at a location offset from a center of the valve flap 34 as shown in at least FIGS. 10-11 so that the valve flap 34 bends at a location closer to the end of the valve flap 34 that is fixed.

The distal housing portion 32 includes a pair of connection protrusions 50, a tube orifice 52, a mating member 54, and a valve seat 56 (see FIG. 14). The connection protrusions 50 are sized to extend through the valve flap 34 and into the connection recesses 42 by the proximal housing portion. The tube orifice 52 is sized to receive the proximal end of the ejector tube 22. The distal housing portion 32 can further include a plurality of barbs 48 that are positioned along the tube orifice surface 52. The barbs 48 are configured to engage an outer surface of the ejector tube 22 to provide an improved connection between the ejector tube assembly 12 and backflow prevention assembly 14. The mating member 54 is sized to engage the first and second mating surfaces 40, 44 of the proximal housing portion 30. The outer diameter surface of the mating member 54 can engage the second mating surface 44 with an interference fit that promotes retention of the proximal and distal housing portions together.

In some arrangements, a connector, fastener, adhesive, or other connecting means can be used to secure the proximal and distal housing portions 30, 32 together in a permanent connection or in a connection arrangement in which the proximal and distal housing portions releasably engaged with each other. In one example, a latching arrangement can be used on the mating surfaces 40, 44 to provide a snap-fit connection between the housing portions 30, 32. An example arrangement includes a pair of protrusions (not shown) are positioned on the surface 40 at 180° spaced apart locations. The protrusions are configured to engage within a pair of recesses (not shown) positioned on the surface 44 also at 1800 spaced apart locations, wherein engagement of the protrusions (not shown) in the recesses (not shown) provide a snap-fit connection between the housing portions 30, 32. The snap-fit connection can be permanent, in that the connection cannot be disconnected without permanent damage to the housing portions 30, 32, or releasable in construction to permit disconnecting of the housing portions 30, 32 without permanent damage being caused.

The use of a single protrusion/recess pair or at least three protrusion/recess pairs can be used to provide a desired connection between the housing portions 30, 32. The protrusion/recess pair can have any configuration and structure that limits relative axial movement of the housing portions 30, 32 after the connection between the protrusion and recess are made.

Figure 20C:
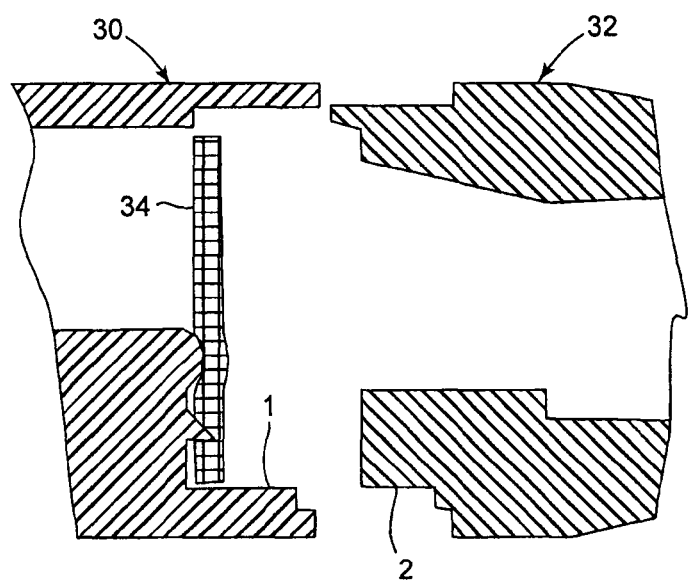
FIG. 20C is a schematic exploded cross-sectional side view of the backflow device shown in FIG. 20A and further including a rib and channel connection arrangement on the proximal and distal housing portions.
Figure 20D:
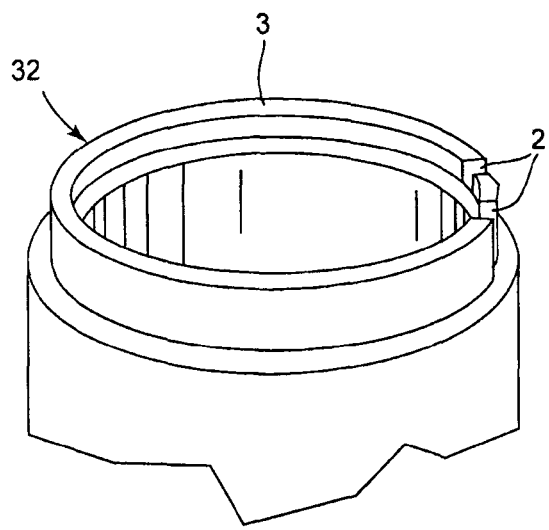
FIG. 20D is a schematic perspective view of the distal housing portion of the backflow device shown in FIG. 20C.
Figure 20E:
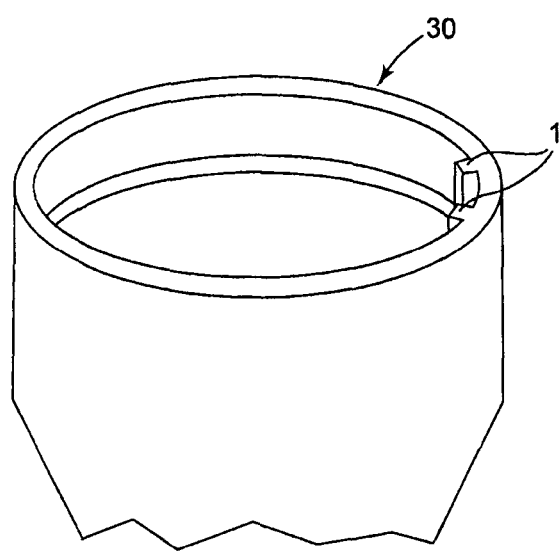
FIG. 20E is a schematic perspective view of the proximal housing portion of the backflow device shown in FIG. 20C.
Figure 31:
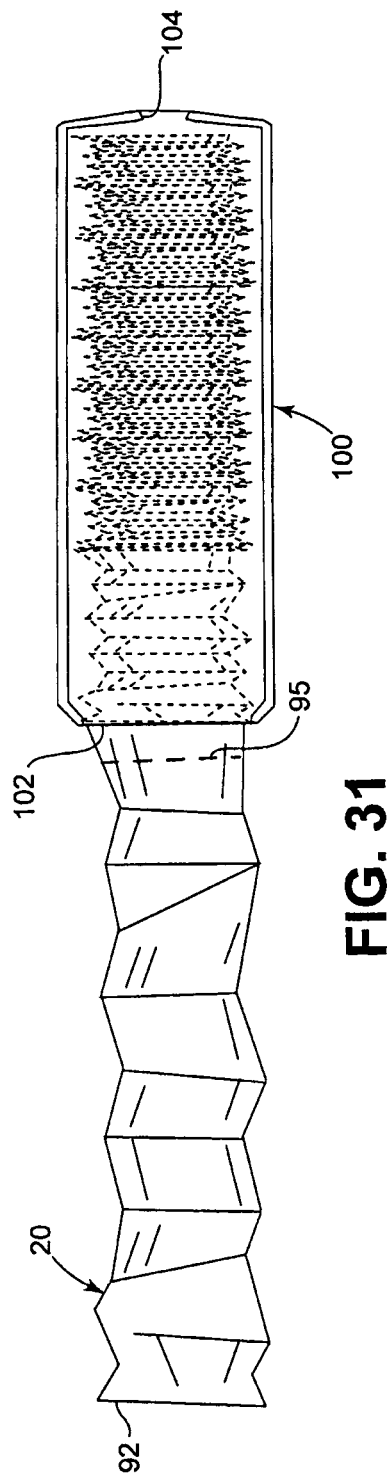
FIG. 31 is a schematic side view of the cover member and housing shown in FIG. 30.

Further, a snap-fit connection such as the protrusion/recess configuration described above, can be used in combination with other connecting and/or aligning features. Referring to FIGS. 20C-E, an example rib 1 and channel 2 arrangement is shown. The rib 1 is positioned on the proximal housing portion 30 and the channel 2 is positioned on the distal housing portion 32. The rib 1 and channel 2 are arranged in an axial direction. The channel 2 is exposed on a proximal end 3 of the distal housing portion 32. The channel 2 and rib 1 can be positioned at any radial location around the circumference of the housing portions 30, 32. The channel 2 and rib 1 can be exchanged to be on the opposite housing portion 30, 32.

More than one pair of channel/rib features can be included on any given pair of housing portions 30, 32. For example, a pair of channel/rib features can be included for each protrusion/recess pair included on a pair of housing portions 30, 32. In one example, a pair of channel/rib features can be positioned radially adjacent to a protrusion/recess pair on the housing portions 30, 32. The channel 2 and rib 1 can be sized to provide an interference fit therebetween when engaged with each other. Engagement of the channel 2 and rib 1 can reduce axial, radial, and rotational movement of the housing portions 30, 32 when the housing portions 30, 32 are connected together with the valve flap 34 captured therebetween.

Other alignment features besides a pair of channel/rib features can be used to help align the housing portions 30, 32 relative to each other when connecting the housing portions 30, 32 together.

The valve flap 34 includes a pair of connection apertures 60, a top end portion 62, a bottom end portion 64, and a diameter D2. The valve flap 34 is sized with a thickness that permits the connection protrusions 50 to extend through the connection aperture 60 and into the connection recesses 42 with the valve flap 34 positioned between the first mating surface 40 of the proximal housing portion 30 and the valve seat 56 of the distal housing portion 32. The diameter D2 of the valve flap 34 is sized no greater than the maximum internal diameter of the valve seat 56.

In other arrangements, the connection protrusions 50 do not extend completely through the connection recesses 42. The connection protrusions 50 can be configured to extend only partially through the thickness of valve flap 34. In other arrangements, the valve flap 34 does not include connection apertures and the connection protrusions 50 are configured to apply a compression force against the valve flap 34 to help retain the valve flap in place. The connection protrusions 50 can have a construction that promotes either concentrated point contact (i.e., a "pinching" contact) with the valve flap 34 or self-penetration of the valve flap 34. FIGS. 20A-C and 24A-B illustrate barb-shaped connection protrusions 50, 250 that engage a valve flap 34, 234 (e.g., see example valve flap 34 shown in FIG. 16F that does not include connection recesses 42). The connection protrusions 50, 250 of FIGS. 20A-C and 24A-B can also be used with a valve flap 34 having connection recesses 42 aligned with the connection protrusions 50, 250. One example connection recess 42 (not shown) for use with connection protrusions 50, 250 shown in FIGS. 20A-C and 24A-B has a shape and size that substantially matches the barb shape of the connection protrusion 50. In still further arrangements, different numbers of connection protrusions and connection recesses can be used to help retain the valve flap. For example, any number from 0 to 3 or more connection protrusions and connection recesses can be used. The connection protrusions 50 can be also be referenced as valve retention members or pins.

The valve flap 34 can have many different configurations (e.g., size and shape) for use with the example proximal and distal housing portions 30, 32 shown in the figures, or variations of those housing portions. FIGS. 16A-18F illustrate several example valve flap configuration. The valve flaps 34 shown in FIGS. 16A-C, 17A-C and 18A-C include contoured cutouts or connection apertures 60 along the bottom end portions 64 of the valve flap 34. The addition of a cutout in the example shown in FIGS. 16A-B can provide easier assembly of the backflow prevention assembly, including insertion of the connection protrusions 50 through the valve flap 34 and into the connection recesses 42. FIG. 16C illustrates an example in which the connection apertures 60 are formed holes at the bottom end portion 64 of the valve flap 34.

The size and shape of the connection apertures 60 can vary as desired to provide, for example, an interference fit over the connection protrusions 50 to ensure tight tolerances. In some arrangements, the connection apertures 60 can have a size greater than the connection protrusions 50 to promote easier assembly and, for example, to ensure free movement of the valve flap 34 relative to the proximal and distal housing portions 30, 32. The contoured cutouts and connection apertures 60 shown in FIGS. 16A-C can be formed using a variety of techniques such as, for example, stamping and molding.

FIGS. 16D-E, 17D-E and 18D-E illustrate some example valve flap configurations that include a protrusion member 68. The protrusion 68 shown in FIG. 16C extends proximally and includes a bottom surface 69 that engages a bottom interior floor surface 31 of the proximal portion 30 (see FIGS. 19A-D). The protrusion 68 provides a function similar to the function of the biasing protrusion 38, but is positioned on the valve flap 34 rather than on the proximal portion 30. The protrusion 68 applies a biasing force against the valve flap 34 in a distal direction to bias the valve flap 34 into a closed position shown in FIG. 19A until a sufficient vacuum force is applied to move the valve flap 34 into the open position shown in FIGS. 19C-D. Typically, the biasing protrusion 38 and protrusion 68 of FIG. 16D are not present in the same backflow prevention assembly 14. Either one of the biasing protrusion 38 (and 138 described below) and the protrusion 68 can be referred to and functional as a valve protrusion that helps bias the valve flap 34 into the closed position.

FIG. 16E illustrates a protrusion 68 having a different construction than the protrusion 68 shown in FIG. 16D. The protrusion 68 of FIG. 16E is configured for use with a biasing protrusion 38 as shown in FIGS. 21A-B. The biasing protrusion 38 in FIGS. 21A-B is truncated to provide a recess 69 adjacent to the first mating surface 40 and the bottom interior floor surface 31 to receive the protrusion 68. When the protrusion 68 is positioned in the recess 69, the protrusion 68 is able to apply a biasing force against the valve flap 34 to hold the valve flap 34 in the closed position shown in FIG. 21A-B.

Many other constructions and combinations of features are possible for the protrusion 68, proximal portion 14, and biasing protrusion 38 in other arrangements. The protrusion 68 can have any desired cross-sectional shape, width, and length. In one example, the protrusion 68 extends across an entire width of the valve flap 34, while in another arrangement the biasing protrusion 68 is a cylindrical shaped member having a rounded distal end.

FIGS. 16F, 17F, 18F illustrate a valve flap 34 that is void of protrusions and connection apertures. The valve flap 34 of FIGS. 16F, 17F, 18F has a generally circular construction and uniform thickness, although many variations of this construction void of protrusions and connection apertures are possible.

When assembled, the backflow prevention assembly 14 provides for opening and closing of a fluid flow path through the backflow prevention assembly determined by a position of the valve flap 34 relative to the valve seats 56. One or both of the biasing protrusion 38 of the proximal housing portion 30 or the protrusion 68 of the valve flap 34 exerts an axially directed force upon the valve flap 34 that biases the valve flap 34 into the closed position before a threshold vacuum force in the proximal housing portion 30 has been met.

Figure 11:
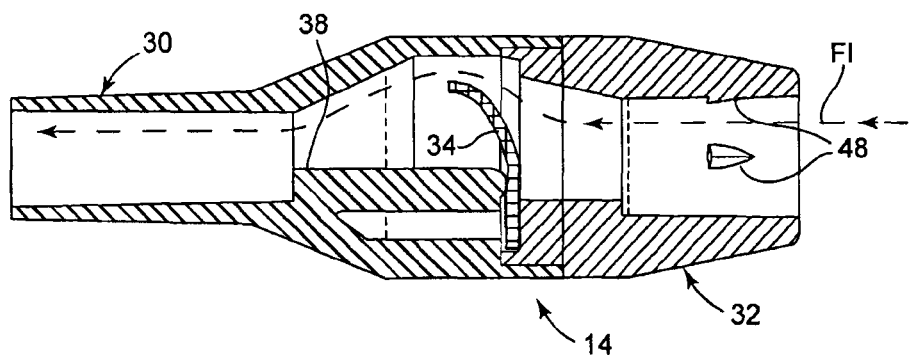
FIG. 11 is a schematic cross-sectional side view of the example backflow device shown in FIG. 10, wherein the valve flap is in an open state.

When a vacuum pressure condition exists in the proximal housing portion 30 (e.g., upon application of a vacuum force at the flow orifice 46) that exceeds a threshold vacuum pressure condition, the top end portion 62 of the valve flap 34 moves proximally as shown in FIG. 11 to provide an open flow condition in the backflow prevention assembly 14. When in the open position, fluid flows along a flow path F1 as shown in FIG. 22 from the tube orifice 52 in the distal housing portion 32 to the tube orifice 52 in the proximal housing portion 30. When the vacuum pressure condition in the proximal housing portion 30 is reduced from the threshold vacuum pressure condition, the valve flap 34 returns to the closed position shown in FIG. 10 upon the biasing force exerted by the biasing protrusion 38. When in the closed position shown in FIG. 10, the backflow prevention assembly 14 substantially prevents backflow of substances positioned in the suction assembly 10 that are located proximal of the valve flap 34.

The threshold vacuum pressure condition is typically less than the atmospheric pressure at sea level (i.e., less than about 15 lb/in² (psi)). In one example, the threshold pressure condition is in the range of about 6 psi to about 12 psi. Another way of measuring vacuum pressure is in inches of Mercury (Hg), wherein all values greater than zero inches of Mercury is a vacuum condition (i.e., less than atmospheric pressure). In one example, the threshold vacuum pressure condition is in the range of about 1 to about 23 inches of Mercury, and more preferably about 6 to about 18 inches of Mercury.

In other arrangements, the valve flap 34 can move under positive fluid pressure forces that are applied to the valve flap 34. For example, the valve flap 34 can be used in a backflow prevent system configuration (not shown) in which valve flap 34 is movable distally into an open position when a positive fluid pressure is applied proximal of the valve flap 34. One such application of this configuration is a liquid soap dispenser that uses the positive pressure of the liquid soap in contact with the valve flap when the dispenser is activated to dispense soap, and when the dispenser is not activated the valve flap moves to the closed position. Maintaining the valve flap in the closed position can help maintain a desired pressure condition proximal of the valve flap that keeps the liquid soap from receding proximally from the backflow prevention device. The amount of positive fluid pressure needed to move the valve flap 34 into an open position can vary depending on many conditions such as, for example, the density of the fluid and the size or shape of the valve flap 34.

The valve flap 34 shown with reference to FIGS. 16B, 17B, 18B includes a bending recess 66 that extends across a width of the valve flap 34 at a location between the top and bottom end portions 62, 64. The valve flap 34 is configured to bend about this bending recess 66 and is held in place between the proximal and distal portions 30, 32 along a bottom portion 64 of the valve flap 34. In other arrangements, the valve flap 34 is held in place by center oriented protrusions (e.g., protrusions 138, 139 shown in FIG. 23) and bending of the valve flap 34 occurs along a centrally oriented bending recess 66.

FIGS. 22 and 23 illustrate another example valve flap 134 that includes a bending recess 66. The valve flap 134 is engaged by a modified biasing protrusion 138 that engages the valve flap 134 along the bending recess 66 to help hold the valve flap 134 in a retained position between proximal and distal portions 130, 132 of the backflow prevention assembly 134 (see FIG. 23). FIG. 23 illustrates the valve flap 134 in a bent state within a backflow prevention assembly 114 upon application of a vacuum pressure in the proximal housing portion 130 that exceeds the threshold vacuum condition. The valve flap 134 can bend about bending recess 66. The valve flap 134 can also bend into a conical or concave shape about the biasing protrusion 138. The distal housing portion 132 can include additional structure such as a retention protrusion 139 that helps hold the valve flap 134 at a fixed location. The biasing protrusion 138 and retention protrusion 139 can have shapes and sizes that promote bending of the valve flap 134 into a conical or concave shape, or bending about the bending recess 66. The bent shape of the valve flap 134 can provide an alternate flow path F2 below or around any other peripheral portion of the valve flap 134. The valve flap 134 can also provide for reduced noise and other operational advantages in some instances.

FIGS. 24A-B illustrate another example backflow prevention assembly 214. The backflow prevention assembly 214 proximal and distal portions 230, 232, a biasing protrusion 238, a retention protrusion 239, and a valve flap 234. The biasing protrusion 238 includes a contoured shape (e.g., a convex shape) at its distal end. The retention protrusion 239 includes a shape at its proximal end that mirrors the contoured shape of the biasing protrusion 238 (e.g., a concave shape). The biasing protrusion 238 can also include a connection protrusion 250 that is arranged to engage the valve flap 234 to help retain the valve flap 234 in a predetermined position when the backflow prevention assembly 214 is assembled. The connection protrusion 250 can have a barb-like shape. Alternatively, the connection protrusion 250 can have any desired shape and size that would be helpful in retaining the valve flap 234 in a desired position.

The contoured shapes of the biasing protrusion 238 and retention protrusion 239, as well as the axial position of the engagement point of the protrusions 238, 239 with the valve flap 234 relative the valve seat 56 tend to bias the valve flap 234 in the closed position.

FIGS. 24C-D illustrate another example backflow prevention assembly 314. The backflow prevention assembly 314 proximal and distal portions 330, 332, a biasing protrusion 338, a retention protrusion 339, and a valve flap 334. The biasing protrusion 338 includes a contoured shape (e.g., a concave shape) at its distal end. The retention protrusion 339 includes a shape at its proximal end that mirrors the contoured shape of the biasing protrusion 338 (e.g., a convex shape). The mirrored shapes of the biasing protrusion 338 and retention protrusion 339 help bias the valve flap 334 into a closed position.

The axial position of the engagement point of the protrusions 338, 339 with the valve flap 234 relative the valve seat 56 tend to bias the valve flap 234 in the open position away from valve seat 56. The contoured shapes of the protrusions 338, 339 tend to bias the valve flap 334 into engagement with the valve seat. The axial point of engagement point of the protrusions 338, 339 with the valve flap 234 relative the valve seat 56 can be modified in this and other embodiments (e.g., assembly 214 discussed above) in combination with various shapes and sizes of the protrusions 338, 339 to vary the performance of valve flap 334.

The valve flaps 134, 234, 334 shown in FIGS. 23-24A-D can be, for example, the valve flap 134 shown in FIG. 22, or any one of the valve flaps 16A-F described above. Other valve flap configurations are possible for use with any of the backflow prevention assemblies described above, include valve flaps that are co-molded or otherwise integrally formed with at least one of the proximal and distal portions (e.g., portions 30, 32) of the backflow prevention assembly.

One advantage related to the valve flaps disclosed with reference to FIGS. 1-24D is that the valve flaps can be manufactured using different manufacturing processes, which could offer simpler and less costly manufacturing process steps for the valve and the overall device. For example, the valve flaps shown in FIGS. 16A and 16B can be merely stamped from a sheet of flexible material rather than being molded as an individual part. The valve flap 34 can also be generated as a separate piece from each of the housing portions 30, 32. As a result, the valve flap 34 can be made from any desired material using any desired process that is not limited in any respect to the manufacturing processes and materials used for the housing portions 30, 32. Preferably, the valve flap comprises a material such as a Silicone or Thermal Plastic Elastomer or other polymeric material. The material selection can be changed to gain different bending responses from the valve flap for different application of the device, and have an effect on properties of, for example, elasticity, stiffness, and moldability. The materials used for the valve flap can also provide a combination of properties that can influence such performance considerations as acoustic vibration.

The ON/OFF valve assembly 16 includes a valve housing 70, a valve member 72, a valve actuator 74, a connection boot 76, a connection orifice 78, and a tube connector 80 (see FIG. 4). The valve actuator 74 is exposed on an exterior of the ON/OFF valve assembly 16 so as to be engaged by a user. The valve actuator 74 moves between a closed orientation shown in FIG. 4 wherein the actuator 74 is positioned at a proximal location and an open position wherein the actuator 74 is moved distally of the valve member 72. Movement of the valve actuator 74 between the proximal and distal positions moves the valve member 72 between a position in which fluid flow through the ON/OFF valve assembly 16 is prohibited, and a position in which the valve member permits fluid flow through the ON/OFF valve assembly 16.

The connection boot 76 is typically removable from the valve housing 70. In some arrangements, the connection boot 76 comprises a rubber or flexible polymeric material that promotes a fluid tight seal with the valve housing 70 and the neck portion 36 of the backflow prevention assembly 14. The structure and material properties of the connection boot 76 also promote relatively easy removal of the connection boot 76 from the valve housing 70, and insertion and removal of the backflow prevention assembly 14 from the connecting orifice 76. Alternative constructions for the connection boot 76 are shown and described in further detail below with reference to FIGS. 25-27D.

The tube connection 80 extends from a proximal end of the valve housing 70. The tube connector is configured to insert into an open end of the vacuum hose 18. A fluid tight connection is provided between the tube connector 80 and the vacuum hose 18. The size of vacuum hose 18 can vary in different applications. For example, the vacuum hose 18 can have an internal diameter (ID) of about 0.125 inches to about 0.5 inches. In another example, the vacuum hose 18 can have an outer diameter (OD) of about 0.25 to about 0.75 inches. Smaller diameter sized vacuum hoses can be referred to as "low volume" vacuum hoses, and larger diameter sized vacuum hoses can be referred to as "high volume" vacuum hoses in some applications. The size of the tube connection 80 and other features of the assembly 10 can be modified for use with any given size of the vacuum hose 18.

The construction of the ON/OFF valve assembly 16 with the valve member 72 positioned generally centrally between the proximal and distal ends of the valve housing 70 makes it possible for there to be suctioned materials lingering within the connection boot 76, portions of the valve housing 70 that are distal of the valve member 72, and ejector tube assembly 12 that are retained there after the valve member 72 is turned to an OFF position. Thus, when the ejector tube assembly 12 and/or backflow prevention assembly 14 is replaced between uses for different patients, there is potential for those retained substances to backflow into the ejector tube assembly 12 and out of the ejector tip 28 before the valve member 72 is again opened to suction those substances out of the suction assembly 10.

When the assembly 10 is in use drawing substances (e.g., fluid) through the assembly under a vacuum pressure applied via the vacuum hose 18, the vacuum pressure can be reduced if the inlet to the ejector tip 28 (see FIG. 3) is blocked. The ejector tip 28 can be blocked when, for example, the ejector tip 28 engages a sealing surface such as a patient's flesh at the suctioning site or an air impervious material (e.g., plastic sheet). When the ejector tip 28 is blocked, the pressure inside assembly 10 is reduced, making it possible for substances in the assembly 10 to flow under gravity forces in the distal direction towards the ejector tip 28. In some limited circumstances, backflow of the substances out of the assembly 10 can occur. The use of the backflow prevention assembly 14 reduces occurrences of such backflow out of the ejector tip 28.

The cover member 20 includes an outer diameter D3, an extended length L2 (see FIG. 8A), an opening restricting member 90, a distal end 92, and a proximal end 94 (see FIGS. 1-4). The cover member 20 is particularly useful for covering at least a portion of the ejector tube assembly 12, at least portions of the backflow prevention assembly 14, and at least portions of the ON/OFF valve assembly 16. In some arrangements, such as the one shown in FIG. 1, the cover member 20 extends from the ejector tube assembly to cover at least a portion of the vacuum hose 18. The cover member 20 can be constructed of a material that is collapsible upon itself such as into the collapsed position shown in FIG. 2, and then able to re-extend into the extended position shown in FIG. 1.

Figure 6:
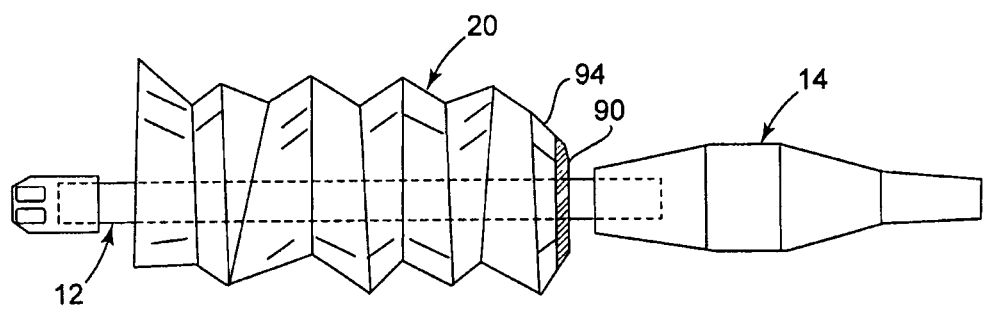
FIG. 6 is a schematic side view of the example assembly shown in FIG. 5, wherein the cover includes a sealed end near the backflow device.
Figure 10:
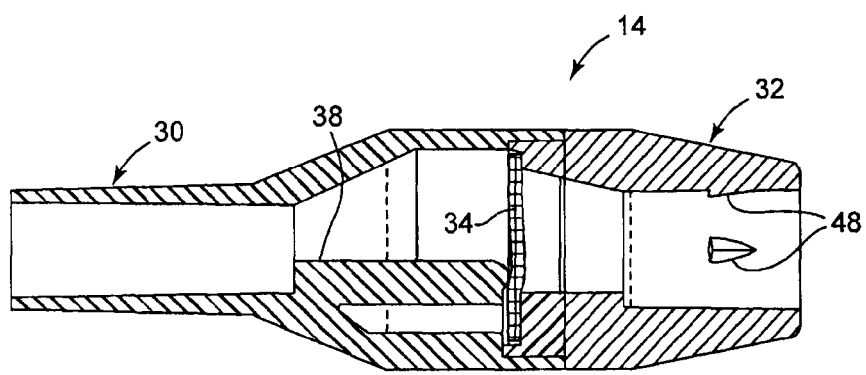
FIG. 10 is a schematic cross-sectional side view of an example backflow device in accordance with the present disclosure, wherein the valve flap is in a closed state.

The opening restricting member 90 can be positioned at the distal end 92 as shown in FIGS. 1-4 to help restrict the size of the distal opening of the cover member 20. Preferably, the opening restricting member 90 helps retain the cover member 20 on the ejector tube 22 without permitting proximal retraction over the backflow prevention assembly 14 and/or the ON/OFF valve assembly 16. The opening restricting member 90 can also provide a limited opening size that prevents distal advancement of the distal end of the cover member 20 beyond the ejector tip 28. In other arrangements, the opening restricting member 90 can be positioned at the proximal end opening of the cover member as shown in FIG. 6. In still further example arrangements, an opening restricting member 90 can be positioned along the length of the cover member 20 at a location between the proximal and distal ends. In other arrangements, multiple opening restricting members 90 can be used at various locations along the length or at proximal and distal ends of the cover member 20. The opening restricting member 90 can comprise an elastic material such as, for example, polyethylene, polyester, latex, or other material such as polyvinyl chloride. In other arrangements, the restricting member 90 is merely a reduced diameter portion of the cover member created by, for example, heat sealing. The opening restricting member 90 can be adjustable in size and shape, or be fixed is size. In one arrangement, the size of the opening restricting member 90 is fixed in size unless permanently deformed by application of a radially outward directed force.

The cover member 20 can comprise a length of tubular structured material. The tubular structure can be generated using an extrusion process, or it can be constructed using a sheet of material that is rolled across its width with side edges sealed together to form the tube shaped structure. The cover member 20 can include a corrugated structure along at least a portion of its length that promotes retracting and extending of the cover member 20 as needed along its entire length to cover certain features of the suction assembly 10, or to provide elongation of the cover member 20 at certain features of the suction assembly 10 such as the ON/OFF valve actuator 74. FIG. 9 illustrates a continuous roll 98 of cover member material. Predefined lengths of the cover member 20 can be indicated by perforations 95, wherein the distance between the distal end 92 and the perforation 95 is in the range of the length L2 shown in FIG. 8A. The length L2 can be in the range of about 8 to about 24 centimeters, and more preferably about 16 to about 22 centimeters. Another means for collecting a continuous length of cover member is described below with reference to FIGS. 34-37.

The cover member 20 can include, in addition to or in place of the opening restricting member 90, a length restricting member 96 that extends along at least a portion of the length L2. FIG. 8B illustrates a single length restricting member 96 extending from the distal end 92 to the proximal end 94 of the cover member 20. FIG. 8C illustrates two separate lengths restricting members 96A, 96B extending between the distal and proximal ends 92, 94. In some arrangements, the length restricting member 96 comprises an elastic material such as, for example, polyethylene, polyester, latex or other plastic materials commonly used polymeric material. In other examples, the length restricting member 96 functions as a stiffening member that maintains a predefined shape that is applied by the user or corresponds to the shape of other features of the suction assembly 10. In still further arrangements, the length restricting member 96 can be replaced with a length extending member that promotes extension of the cover member 20 to its maximum length and resists bunching or restricting of the cover member 20 along its length (e.g., the restricted arrangement shown in FIG. 2).

The length restricting members 96A, 96B can be separate members that extend along the length L2, or can be a continuous member that extends around an entire outer periphery of the cover member 20. In still further arrangements, the members 96A, 96B can replace portions of the cover member 20. The opening restricting member 90 and length restricting members 96 can be secured to the cover member 20 in a separate manufacturing step, can be co-molded or co-extruded with the cover member 20, or attached in any way desired, for example, an end user.

In the application of a dental or medical environment, a primary advantage of the cover member 20 is to permit the user to operate the ON/OFF valve 16 without having to remove their gloves and while maintaining sanitary conditions. Currently, users working with a medical or dental patient wear gloves to promote sanitation. The user often operates the uncovered and possibly contaminated ON/OFF valve without taking off their gloves. In some cases some users will go through the trouble of removing their gloves after touching a contaminated ON/OFF valve. If the gloves are removed, then it takes time to take them off and put back on a new pair. In some cases, the gloves are wet and sticking and a new pair is required to continue working on the patient.

The Example Connection Boot of FIGS. 25-28D

The connection boot 76 used with the ON/OFF assembly 16 can be modified to include a backflow prevention valve for use in addition to or in place of the backflow prevention assembly 14 described above with reference to FIGS. 1-25. FIG. 27 illustrates an example boot valve assembly 82 shown assembled with an ejector tube assembly 12. The boot valve assembly 82 includes an adapter 84 and a valve member 86. The adapter 84 includes a connecting orifice 78, a plurality of barb members 48 extending into the connecting orifice 78, and a proximal end surface that defines a valve seat 85. (See FIG. 28.) The barbs 48 help retain the proximal end of the ejector tube 22 within the adapter 84. The valve seat 85 provides a stop surface that defines a distal most axial position of the valve member 86 when in the closed position. The valve member 86 extends from an internal sidewall of the connection boot 76.

The examples shown in FIGS. 25-28C include a valve member that is integral with a sidewall of the connection boot 76. FIGS. 25A, 26A show the valve member 86 biased in the distal direction before assembly. When assembled, the adapter 84 in the example of FIG. 25 and the ejector tube assembly 12 in the example of FIG. 26 move the valve member 86 into a closed position, whereby the valve member 86 imposes a biasing force in the distal direction. This distally directed biasing force prevents the valve member 86 from moving proximally into an open position until a threshold vacuum pressure condition is exceeded.

Variations of the boot valve assembly 82 shown in FIGS. 25 and 26 are included in FIGS. 27A-C and 28A-C. In each of these examples, the connection boot 76 is configured such that the adapter 84 is not needed. The proximal end of the ejector tube 22 can be secured directly to the connecting orifice 78 of the connection boot 76. In FIGS. 27A-B, the valve member 86 is positioned at a proximal end of the connecting orifice 78 so as to be positioned directly adjacent to the proximal most end of the ejector tube 22 when the ejector tube 22 is inserted in the connecting orifice 78. FIG. 27C includes a valve member 86 that is positioned spaced proximal of the connecting orifice 78 so as to be functionally closer to the valve housing of the ON/OFF valve assembly.

FIGS. 27D, 28D illustrates a further example in which a removable valve assembly 88 is positioned within the connection boot 76. The removable valve assembly 88 includes first and second portions 87, 89 with the valve member 86 captured therebetween. The outer dimensions of the removable valve assembly 88 match the internal dimensions of the connection boot 76 thereby helping maintain the removable valve assembly 88 in a desired axial position within the connection boot 76. The valve seats and related structure of the removable valve assembly 88 is similar in some respects to features of the backflow prevention assembly housing portions and valve flap described above with reference to FIGS. 10-24D.

Any of the arrangements discussed above with reference to the attached figures that include an ejector tube can be constructed as a single piece object. For example, the combination of the ejector tube assembly 12 with the backflow prevention device 14 shown in FIGS. 1-4 can include a combined, single piece construction of the ejector tube assembly 10 with the distal housing portion 32 or another portion of the backflow prevention device 14. In another example, the ejector tube assembly 12 shown in FIGS. 25 and 26 can be formed as a single piece with the connection boot 76, adapter 84, or a different distal portion of the ON/OFF valve assembly 16.

Additional Cover Member Examples of FIGS. 29-33

The example cover members described herein can be used in combination with various features of the suction assembly 10 individually or in subassemblies. For example, the cover member 20 can be used in a subassemblies with the ejector tube assembly 12. FIG. 7 illustrates such a subassembly. In the subassembly of FIG. 7, the opening restriction member 90 helps retain the cover member 20 along the length of the ejector tube 22. The proximal end of the ejector tube 22 can be secured directly to the connection boot 76 of the ON/OFF valve assembly 16 as shown in FIG. 29. The cover member 20 can be extended to cover at least a portion of the ejector tube 22 and substantially all of the ON/OFF valve assembly 16. Portions of the cover member 20 can also extend proximally beyond the ON/OFF valve assembly 16 to cover at least portions of the vacuum hose 18.

Figure 5:
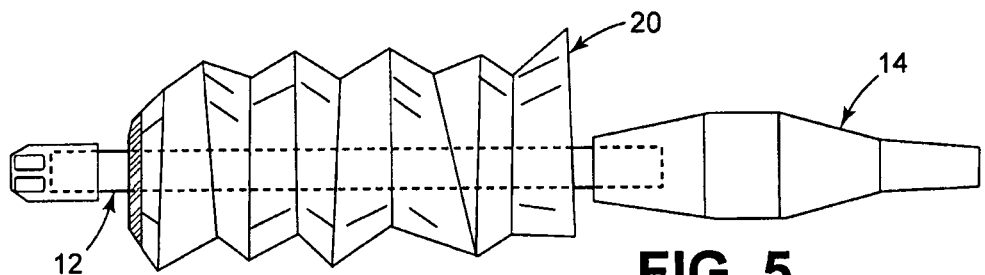
FIG. 5 is a schematic side view of an example assembly in accordance with the present disclosure that includes an ejector tube, backflow device and cover, wherein the cover includes a sealed end near the ejector tip.

In another example arrangement, the cover member is provided with a subassembly that includes the ejector tube assembly 12 and the backflow prevention assembly 14 as shown in FIGS. 5 and 6. The proximal end of the ejector tube 22 is secured directly to the distal end of the backflow prevention assembly 14 (see also FIGS. 1-4). In this arrangement, the opening restrictor member 90 helps retain either the distal or the proximal end of the cover member 20 along the length of the ejector tube 22 between the ejector tube 28 and the backflow prevention assembly 14.

Subassemblies of the cover member with the ejector tube assembly and/or the backflow prevention assembly can be provided as disposable parts that are easily replaceable when used with the ON/OFF valve assembly 16. The cover member 20 provides a physical boundary between the user and the ON/OFF valve assembly 16 and/or the backflow prevention assembly 14, which may have been touched or exposed to unsanitary conditions between uses of the suction assembly 10 on different patients. A primary purpose of the cover member 20 is to provide a barrier that will become contaminated when used. The cover member 20 captures unsanitized portions of the suction assembly 10 within the interior of the cover and provides a sanitary surface on the exterior of the cover. The cover prevents the user of the ON/OFF valve assembly 16 from coming in contact with the surface of the ON/OFF valve assembly 16, which may be contaminated. The cover member 20 also inhibits transfer of contaminates on the user's hands or gloves to the ON/OFF valve assembly 16 and other features within the interior of the cover member 20. The cover member 20 may become contaminated with fluids, bacteria and other contaminates associated with the patient during use of the suction assembly 10. Each time the cover member 20 is removed from the suction assembly 10, those contaminates that have been transferred to the exterior or interior of the cover member 20 are removed with the cover member 20, and therefore removed from possible transfer to the next patient by way of the user.

Now referring to FIGS. 30-33, an alternative cover member configuration and retention structure is now described. FIG. 30 illustrates a cover member housing 100 that retains within it a continuous length of cover member 20 that is restricted into a contracted state. The cover member housing 100 includes distal and proximal openings 102, 104. The proximal opening 104 is sized to extend the vacuum hose 18 through an interior of the cover member housing 100 and into engagement with the tube connector 80 of the ON/OFF valve assembly 16. The cover member housing 100 includes an internal dimension 108 that can be at least as great as a maximum diameter D3 of the cover member 20. The distal opening 102 is shown in FIGS. 30-33 being about the same as dimension D3 of the cover member 20. In other arrangements, the distal opening 102 can have a smaller size and can be as small as the outer diameter of the vacuum hose 18 plus two times the thickness of the cover member material in order to permit removal of the cover member 20 from between the vacuum hose 18 and opening 102.

The cover member housing 100 is shown in FIG. 30 positioned completely proximal of the proximal end of ON/OFF valve assembly 16. In other arrangements, the cover member housing 100 can be positioned distally so at least a portion of the ON/OFF valve assembly 16 is positioned internal of the cover member housing 100.

Figure 33:
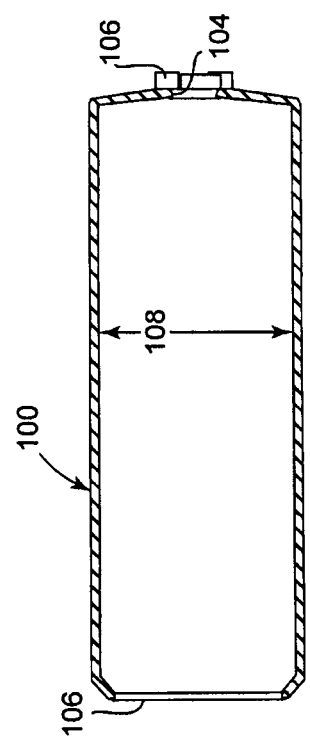
FIG. 33 is a schematic cross-sectional side view of another example side member housing in accordance with the present disclosure, the side member housing including a fastener member to hold a position of the side member housing member relative to the ON/OFF valve.

The cover member housing 100 can further include a connector 106 at either the distal or proximal opening 102, 104. FIG. 33 illustrates the connector 106 adjacent the proximal opening 104. The connector 106 can be used to secure the cover member housing 100 to the vacuum hose 18 at a predefined location along the length of the vacuum hose 18. In other arrangements, the connector 106 can be used to secure the cover member housing 100 to other features such as, for example, the ON/OFF valve housing 70 or other features of the suction assembly 10.

The cover member housing 100 can further include a cutting member (not shown) positioned at, for example, a location adjacent the distal opening 102 to help in cutting off a length of the cover member 20 that has been drawn distally out from the cover member housing 100. As mentioned above, the cover member 20 can include perforations 95 at positions along its length to assist in removing a desired amount of the cover member length that has been drawn distally out of the cover member housing 100. In some arrangements, the cover member 20 can include an opening restricting member 90 positioned on at least one of a proximal and distal side of the perforations 95 to provide restriction of one or both ends of the cover member 20 that has been drawn out of the cover member housing 100.

Figure 32:
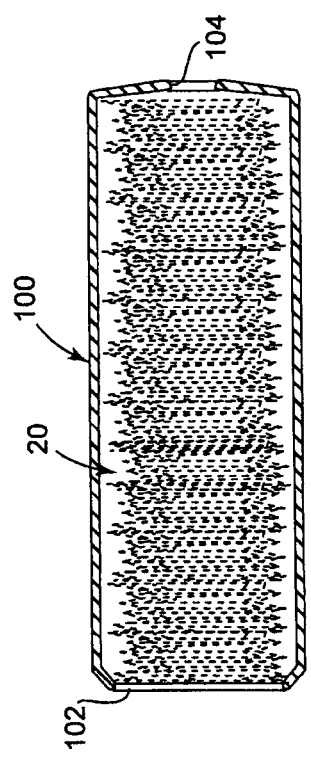
FIG. 32 is a schematic cross-sectional side view of the side member and housing shown in FIG. 31, wherein the cover member is completely retained in the housing.

FIG. 32 illustrates a continuous length of cover member 20 compressed within the cover member housing 100. The continuous length of cover member 20 supplied to the housing 100 can be supplied from, for example, the roll 98 of cover member 20 shown in FIG. 9. The cover member housing can be provided with enough length of cover member 20 for a predetermined number of lengths L2 of cover member. The predetermined number of lengths L2 can be, for example, the number needed for a certain number of uses of the suction assembly 10 for a given number of patients in a certain time frame. For example, the housing 100 can hold the number of lengths L2 of cover member 20 for use in a half day, full day, week, or month's worth of patients being treated. The total length of cover member 20 compressed within an particular configuration of the cover member housing 100 can vary depending on, for example, the material diameter (D3), whether or not opening restricting members or length restricting members are used with the cover member 20, and other considerations related to the construction of the cover member 20. The amount of cover member material held within the cover member housing 100 is also dependent upon, for example, the internal dimensions including, for example, the internal diameter and internal length of the cover member housing 100.

In some arrangements, the cover member housing 100 can be permanently attached to the vacuum line. The cover member housing can be loaded with refill cartridges or refill lengths of the cover tubing as desired in any of the above described arrangements. The cover member housing 100 can also be constructed as a two piece design that can be disassembled in part to refill the housing and then re-assembled for use.

CONCLUSION

One aspect of the present disclosure relates to a vacuum backflow prevention system that includes a fluid ejector tube and a backflow prevention device. The fluid ejector tube is adapted for insertion into a patient's mouth. The backflow prevention device includes a distal portion, a proximal portion, a valve member, and a valve protrusion. The distal portion defines a valve seat portion and an inlet and is operable connected to the fluid ejector tube. The proximal portion defines an outlet and is configured for operative connection to a vacuum source and to the distal portion. The valve member is captured between the proximal and distal portions. The valve member is moveable from a first position substantially blocking fluid flow between the inlet and the outlet, and a second position wherein a portion of the valve member is moved in a direction toward the outlet to permit fluid to flow from the inlet to the outlet under a vacuum condition applied by the vacuum source at the outlet. The valve protrusion is configured to bias the valve member into the first position.

The valve protrusion maintains a fixed position relative to the distal and proximal portions of the backflow prevention device.

Another aspect of the present disclosure relates to a vacuum suction system that includes an ON/OFF valve assembly, a backflow prevention device, and a fluid ejector tube. The ON/OFF valve assembly includes an ON/OFF valve housing, an ON/OFF valve positioned in the ON/OFF housing, an ON/OFF valve inlet, and an ON/OFF valve outlet. The backflow prevention device includes a distal portion defining a backflow inlet, a proximal portion defining a backflow outlet, and a valve member. The valve member is captured between the distal and proximal portions. A portion of the valve member is configured to move between a closed position and an open position upon application of a predetermined vacuum condition at the backflow outlet. The valve biasing member is configured to remain in the closed position in the absence of the predetermined vacuum condition. The backflow outlet is secured in fluid communication with the ON/OFF valve inlet, wherein the ON/OFF valve is configured to control application of the predetermined vacuum condition at the backflow outlet. The fluid ejector tube is in fluid communication with the distal portion of the backflow prevention device.

A still further aspect of the present disclosure relates to a backflow prevention device that includes a distal portion, a proximal portion, and a valve member. The distal portion defines a distal opening. The proximal portion defines a proximal opening. The valve member is positioned between the distal portion and the proximal portion. The valve member is automatically moveable from a first position substantially blocking fluid flow between the inlet and the outlet, and a second position wherein a portion of the valve member is moved toward the proximal opening to permit fluid to flow between the distal opening and the proximal open upon application of a predetermined fluid force to the valve member.

Another aspect of the present disclosure relates to a disposable cover member assembly that is adapted for use with a suction assembly. The cover member assembly includes a length of tubular shaped cover member and a cover member housing. The cover member defines a cover member interior. The cover member housing defines a proximal opening, a distal opening, and a housing cavity. A portion of the suction assembly extends inside the housing cavity through the proximal opening and the distal opening and through the cover member interior. The cover member is configured to be drawn out of the distal opening to cover a portion of the suction assembly that is positioned distal of the cover member housing.

Another aspect of the present disclosure relates to a method of assembling a fluid ejector system. The fluid ejector system includes a fluid ejector tube, a backflow prevention device, and a cover member. The backflow prevention device includes a valve member that provides one-way flow of fluid through the backflow prevention device. The method steps includes inserting a portion of the fluid ejector tube through the cover member, and engaging a proximal end of the fluid ejector tube with a distal end of the backflow prevention device, wherein a portion of the cover member is captured between a distal end of the fluid ejector tube and the backflow prevention device, and the cover member substantially covers the backflow prevention device.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment. Therefore, the spirit and scope of the appended claims should not be limited to the description of the preferred versions contained herein.

We claim:

1. A vacuum backflow prevention system, comprising:
   a fluid ejector tube adapted for insertion into a patient's mouth;
   a backflow prevention device, comprising:
      a distal portion defining a valve seat portion and an inlet, the distal portion configured for operative connection to the fluid ejector tube;
      a proximal portion defining an outlet and a valve contact surface, the proximal portion configured for operative connection to a vacuum source and to the distal portion;
      a valve member being captured between the valve contact surface of the proximal portion and the valve seat of the distal portion at a first end along a portion of a peripheral edge of the valve member, the valve member being moveable from a first position substantially blocking fluid flow between the inlet and the outlet, and a second position wherein a second end of the valve member opposite the first end is moved in a direction toward the outlet to permit fluid to flow from the inlet to the outlet under a vacuum condition applied by the vacuum source at the outlet, the valve member being configured to bend at a location radially inward from the peripheral edge and at a location spaced closer to the first end than the second end; and
   a valve protrusion positioned on a proximal side of the valve member in contact with the proximal portion of the backflow prevention device, the valve protrusion being configured to bias the valve member into the first position.

2. The system of claim 1, wherein the valve member is disk-shaped.

3. The system of claim 1, wherein the valve member comprises a flexible polymeric material.

4. The system of claim 1, further comprising a valve retention member positioned between the valve seat and the proximal portion, the valve retention member configured to retain the valve member in a predetermined orientation.

5. The system of claim 4, wherein the valve retention member extends through the valve member and engages in a recess in one of the proximal and distal portions.

6. The system of claim 1, wherein the valve protrusion is integral with the proximal portion, and a portion of the valve protrusion extends distally into engagement with the valve member.

7. The system of claim 1, wherein the valve protrusion is integral with the valve member, the valve protrusion being arranged to extend proximally from the valve member and into engagement with the proximal portion.

8. The system of claim 1, further comprising a cover member, the cover member defining an internal space sized to receive at least the backflow prevention device therein.

9. The system of claim 1, wherein the cover member is secured to the fluid ejector tube at a location between a distal tip of the fluid ejector tube and the distal portion of the backflow prevention device.

10. A vacuum suction system, comprising:
an ON/OFF valve assembly comprising a ON/OFF valve housing, an ON/OFF valve positioned in the ON/OFF housing, an ON/OFF valve inlet, and an ON/OFF valve outlet;
a backflow prevention device comprising a distal portion defining a backflow inlet and a valve seat, a proximal portion defining a backflow outlet and a valve contact surface, and a valve member having a sealing portion that contacts the valve seat to form a seal, the valve member being captured within the valve seat between the distal portion and the valve contact surface of the proximal portion at a first end along a portion of a peripheral edge of the valve member radially inward from the sealing portion, an opposite second end of the valve member being configured to move between a closed position and an open position upon application of a predetermined vacuum condition at the backflow outlet, the valve member being biased toward the backflow inlet to remain in the closed position in the absence of the predetermined vacuum condition and being configured to bend at a location spaced radially inward from the peripheral edge closer to the first end than the second end, the backflow outlet secured in fluid communication with the ON/OFF valve inlet, the ON/OFF valve being configured to control application of the predetermined vacuum condition at the backflow outlet; and
a fluid ejector tube in fluid communication with the distal portion of the backflow prevention device.

11. The system of claim 10, wherein the backflow prevention device further includes a valve biasing member, the valve biasing member configured to apply a force to the valve member to bias the valve member into the closed position.

12. The system of claim 10, further comprising a cover member, the cover member defining an internal space sized to receive at least the ON/OFF valve assembly.

13. The system of claim 10, wherein the backflow prevention device further includes a valve retention member positioned between the distal portion and the proximal portion, the valve retention member configured to retain the valve member in a predetermined orientation.

14. A backflow prevention device, comprising:
a distal portion defining a distal opening at a distal end thereof and a valve seat at a proximal end thereof;
a proximal portion defining a proximal opening at a proximal end thereof and a valve contact surface at a distal end thereof; and
a valve member positioned at a location within the valve seat between the distal portion and the valve contact surface of the proximal portion with a first end of the valve member being fixed along a perimeter of the valve member, the valve member being biased toward the distal opening, the valve member being automatically moveable from a first position substantially blocking fluid flow between the inlet and the outlet, and a second position wherein a second end of the valve member opposite the first end is moved toward the proximal opening to permit fluid to flow between the distal opening and the proximal opening upon application of a predetermined fluid force to the valve member, the valve member being configured to bend at a location radially inward from the perimeter portion and at a location spaced closer to the first end than the second end.

15. The device of claim 14, further comprising at least one valve retention member positioned between the proximal portion and the distal portion, the at least one valve retention member configured to engage the valve member to retain the valve member in a predetermined orientation relative to the proximal portion and the distal portion.

16. The device of claim 15, wherein the at least one valve retention member includes a connection protrusion that extends at least partially through a thickness of the valve member.

17. The device of claim 16, wherein one of the proximal portion and distal portion defines at least one connection recess, the at least one connection recess configured to receive the at least one connection protrusion.

18. The device of claim 16, wherein the valve member includes a cut out portion that extends from a periphery of the valve member radially inward to a location in alignment with the at least one connection protrusion.

19. The device of claim 14, wherein the predetermined fluid force is a vacuum force applied at the proximal opening.

20. The device of claim 14, wherein the predetermined fluid force is a positive pressure force applied at the distal opening.

21. The device of claim 14, wherein one of the proximal portion and the distal portion includes an axially aligned rib, and the other of the proximal portion and the distal portion including an axially aligned channel sized to receive the rib when the proximal and distal portions are connected together.

22. The system of claim 1, wherein the inlet of the distal portion includes a bore having a plurality of attachment members protruding radially inward.

23. The system of claim 1, wherein the valve protrusion contacts the valve member at a location radially offset from a center of the valve member.

24. The system of claim 22, wherein the plurality of attachment members have a barb shape.

25. The system of claim 22, wherein the plurality of attachment members are configured to engage the fluid ejector tube to create a positive connection between the fluid ejector tube and the backflow prevention device.

26. The system of claim 10, wherein the backflow inlet of the distal portion includes a bore and a plurality of attachment members positioned in the bore and protruding radially inward.

27. The system of claim 26, wherein the plurality of attachment members have a barb construction.

28. The device of claim 14, wherein the distal opening of the distal portion includes a bore and a plurality of attachment members positioned in the bore and protruding radially inward.

29. A vacuum suction system, comprising:
a backflow prevention device comprising:
a distal portion defining a backflow inlet and a valve seat;
a proximal portion defining a backflow outlet and a valve contact surface;
a valve member captured within the valve seat and having a sealing portion that contacts the valve seat to form a seal, the valve member being held in place with at least one retaining member that contacts the valve member at location spaced radially inward from the sealing portion and a peripheral edge of the valve member at a first end, an opposite second end of the valve member being configured to move between a closed position and an open position upon application of a predetermined vacuum condition at the backflow outlet, the valve member being configured to remain in the closed position in the absence of the predetermined vacuum condition and being configured to bend at a location spaced radially inward from the peripheral edge closer to the first end than the second end;

an ON/OFF valve assembly comprising a ON/OFF valve housing, an ON/OFF valve positioned in the ON/OFF housing, an ON/OFF valve inlet, and an ON/OFF valve outlet, the ON/OFF valve inlet being secured in fluid communication with the backflow outlet, the ON/OFF valve being configured to control application of the predetermined vacuum condition at the backflow outlet;

a fluid ejector tube in fluid communication with the distal portion of the backflow prevention device.

30. The system of claim 29, wherein the at least one retaining member includes at least one connection protrusion that extends through the valve member.

31. The system of claim 29, wherein the at least one retaining member includes at least one connection protrusion configured to provide at least one point contact with the valve member.

32. The system of claim 31, wherein the at least one connection protrusion includes a barb shaped member.

* * * * *